United States Patent [19]

Pittet et al.

[11] 4,048,201
[45] Sept. 13, 1977

[54] NOVEL ENOL ESTERS

[75] Inventors: Alan Owen Pittet, Atlantic Highlands; Erich Manfred Klaiber, Neptune; Manfred Hugo Vock, Locust, all of N.J.; Edward J. Shuster, Brooklyn, N.Y.; Joaquin Vinals, Red Bank, N.J.

[73] Assignee: International Flavors & Fragrances Inc., New York, N.Y.

[21] Appl. No.: 723,536

[22] Filed: Sept. 15, 1976

Related U.S. Application Data

[60] Division of Ser. No. 662,820, March 1, 1976, Pat. No. 4,000,329, which is a continuation-in-part of Ser. No. 620,355, Oct. 7, 1975, Pat. No. 4,000,090, which is a continuation-in-part of Ser. No. 507,412, Sept. 19, 1974, Pat. No. 3,940,499.

[51] Int. Cl.² .................................................. C09F 5/08
[52] U.S. Cl. ...................................... 260/410; 252/522; 560/231
[58] Field of Search ............... 260/488 A, 488 R, 489, 260/410; 252/522

[56] References Cited
U.S. PATENT DOCUMENTS

| 2,957,933 | 10/1960 | Pommer et al. | 260/598 X |
| 3,899,597 | 8/1975 | Mookherjle et al. | 252/522 X |

Primary Examiner—Patrick P. Garvin
Assistant Examiner—John F. Niebling
Attorney, Agent, or Firm—Arthur L. Liberman; Harold Haidt; Franklin D. Wolffe

[57] ABSTRACT

Processes and compositions are described for the use in foodstuff, chewing gum, toothpaste and medicinal product flavor and aroma, tobacco flavor and aroma and perfume aroma augmenting, modifying, enhancing and imparting compositions and as foodstuff, chewing gum, toothpaste, medicinal product tobacco, perfume and perfumed article aroma imparting materials of one or more alkyl side chain methyl substituted or unsubstituted 2,2,6-trimethyl-1-cyclohexen-1-vinyl alkanoates (hereinafter referred to as "enol esters") having the generic structure:

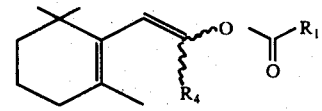

(which structure is intended to cover both the "cis" and the "trans" isomers thereof) wherein $R_1$ is $C_1$-$C_{11}$ alkyl and $R_4$ is hydrogen or methyl.

9 Claims, 36 Drawing Figures

EXAMPLE XXXIV

GLC PROFILE OF REACTION PRODUCT CONTAINING "CIS" AND "TRANS" ISOMERS

EXAMPLE XXXIV

GC-MS PROFILE OF REACTION PRODUCT CONTAINING "CIS" AND "TRANS" ISOMERS

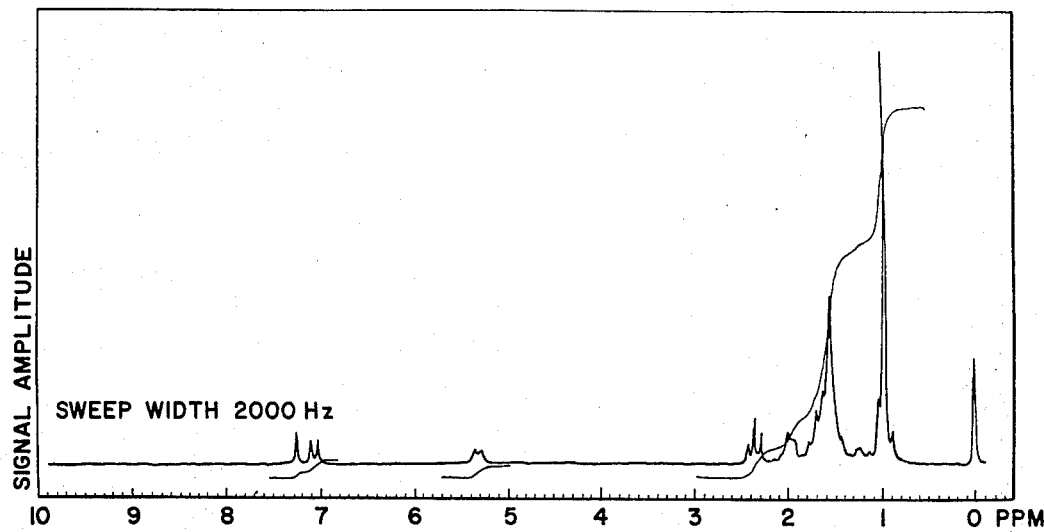
FIG. 3
EXAMPLE XXXIV
FIG. 4
EXAMPLE XXXIV
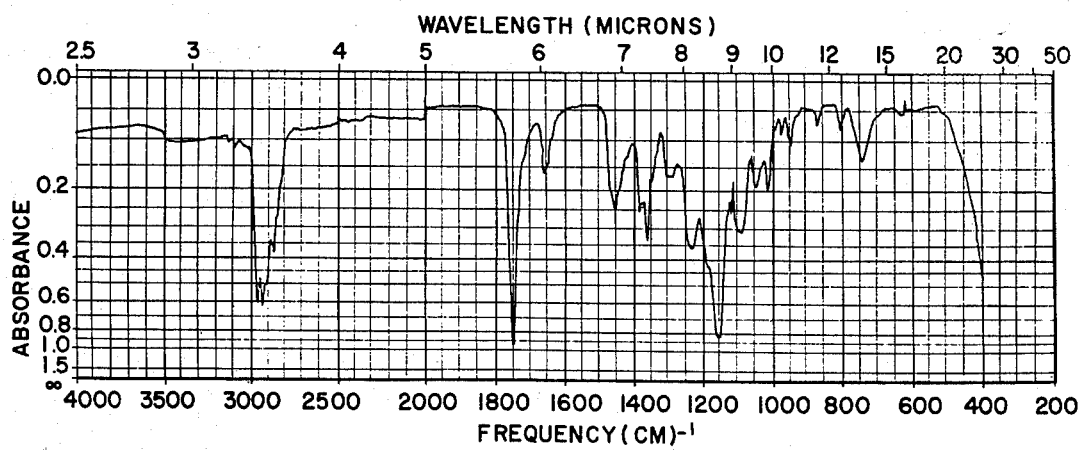

EXAMPLE XXXIV

IR SPECTRUM OF "TRANS" ISOMER OF ENOL BUTYRATE

EXAMPLE XXXIV

NMR SPECTRUM OF "TRANS" ISOMER OF ENOL BUTYRATE

EXAMPLE XXXVI

GLC PROFILE OF REACTION PRODUCT CONTAINING "TRANS" ISOMER OF ENOL BUTYRATE

EXAMPLE XXXV

GLC PROFILE OF REACTION PRODUCT CONTAINING "CIS" AND "TRANS" ISOMERS OF ENOL BUTYRATE.

EXAMPLE XXXVII
GLC PROFILE OF ENOL ISOBUTYRATE

EXAMPLE XXXVI
GC-MS PROFILE OF REACTION PRODUCT CONTAINING "TRANS" ISOMER OF ENOL BUTYRATE

EXAMPLE XXXVII

GC-MS PROFILE OF ENOL ISOBUTYRATE

PARENT PEAK (236)

EXAMPLE XXXVII

NMR SPECTRUM FOR "CIS" ISOMER OF ENOL ISOBUTYRATE

SWEEP WIDTH 2000 Hz

EXAMPLE XXXVIII

GLC PROFILE-CRUDE CONTAINING ENOL n-OCTANOATE

EXAMPLE XXXVII
NMR SPECTRUM FOR "TRANS" ISOMER OF ENOL ISOBUTYRATE

EXAMPLE XXXVIII

GC-MS PROFILE OF ENOL n-OCTANOATE

EXAMPLE XXXVIII

NMR SPECTRUM "TRANS" ISOMER OF ENOL n-OCTANOATE

SWEEP WIDTH 2000 Hz

GLC PROFILE OF ENOL PROPIONATE

EXAMPLE XLVI

NMR SPECTRUM

"CIS" ISOMER OF ENOL OCTANOATE

EXAMPLE XXXVIII

EXAMPLE XLIX

GLC PROFILE OF ENOL ACETATE (REACTION USING BENZENE SOLVENT)

EXAMPLE XLVIII

GLC PROFILE OF ENOL ACETATE

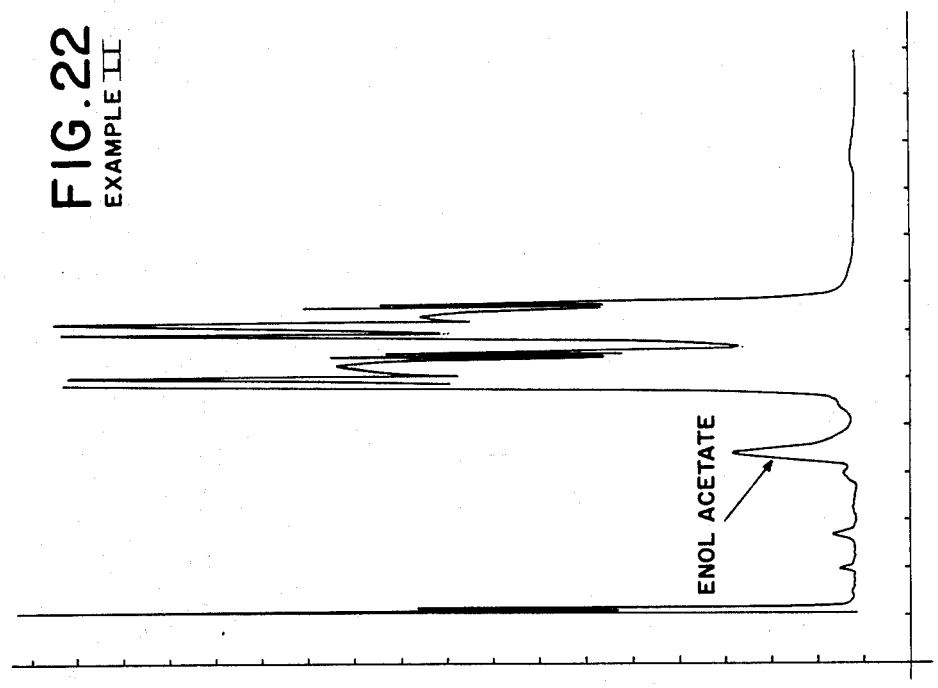
FIG. 22 EXAMPLE II
GLC PROFILE OF ENOL ACETATE
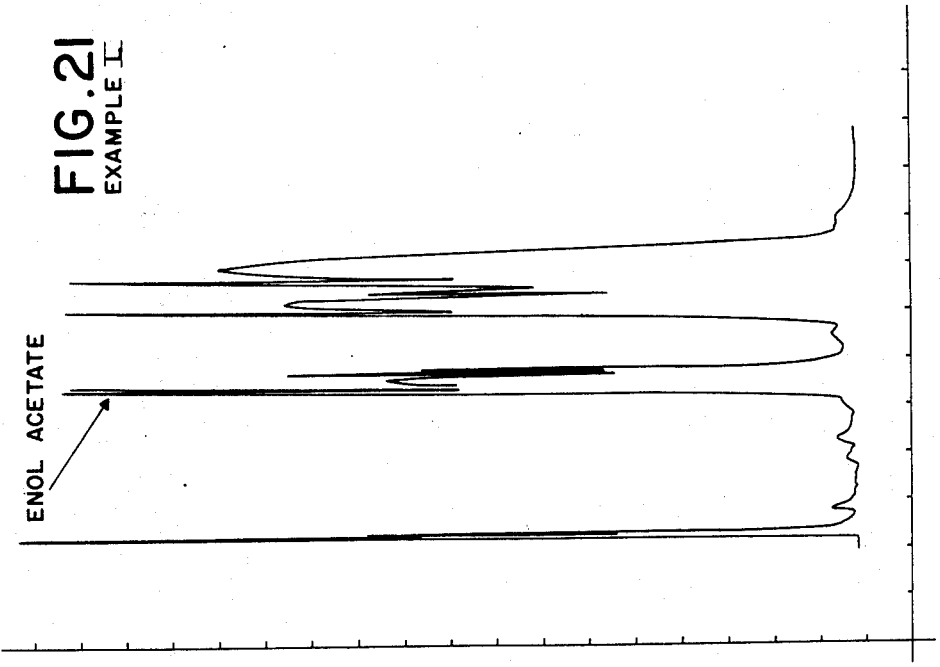
FIG. 21 EXAMPLE I
GLC PROFILE OF ENOL ACETATE

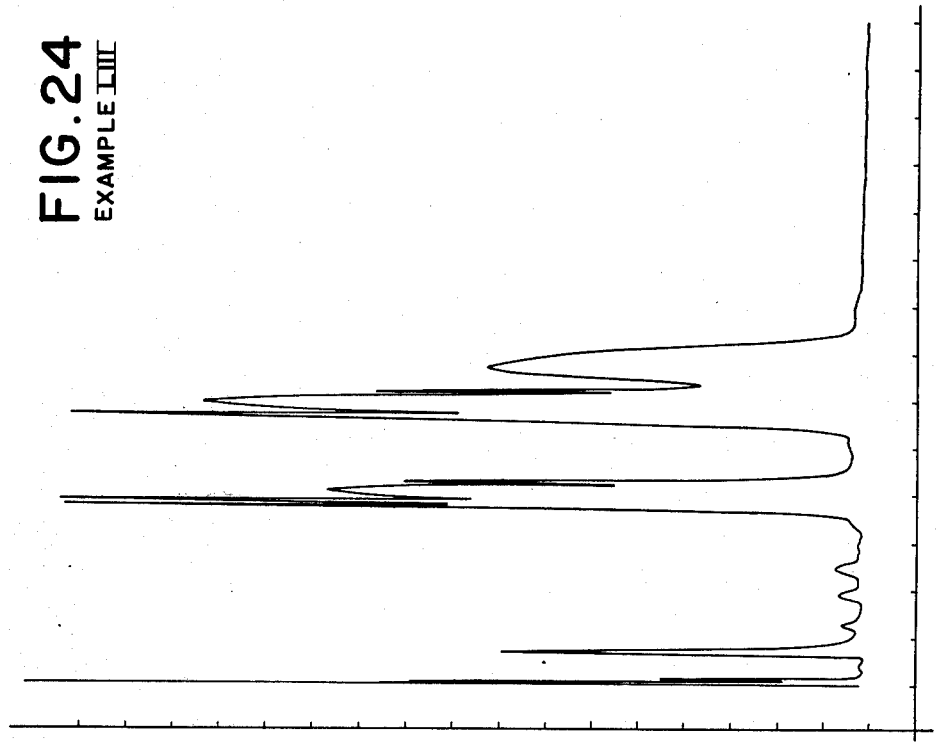
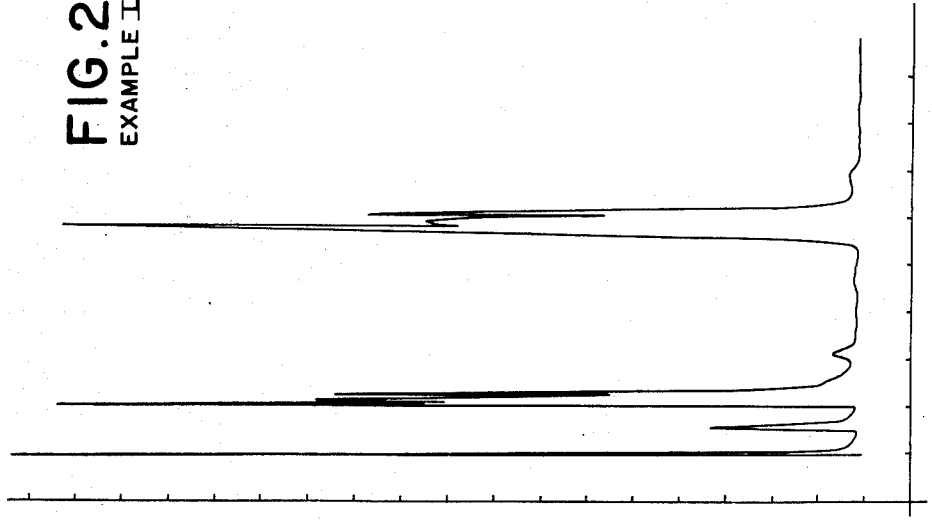

EXAMPLE IV
GLC PROFILE (REACTION USING BENZENE SOLVENT)

EXAMPLE IV
GLC PROFILE (REACTION USING DMF SOLVENT)

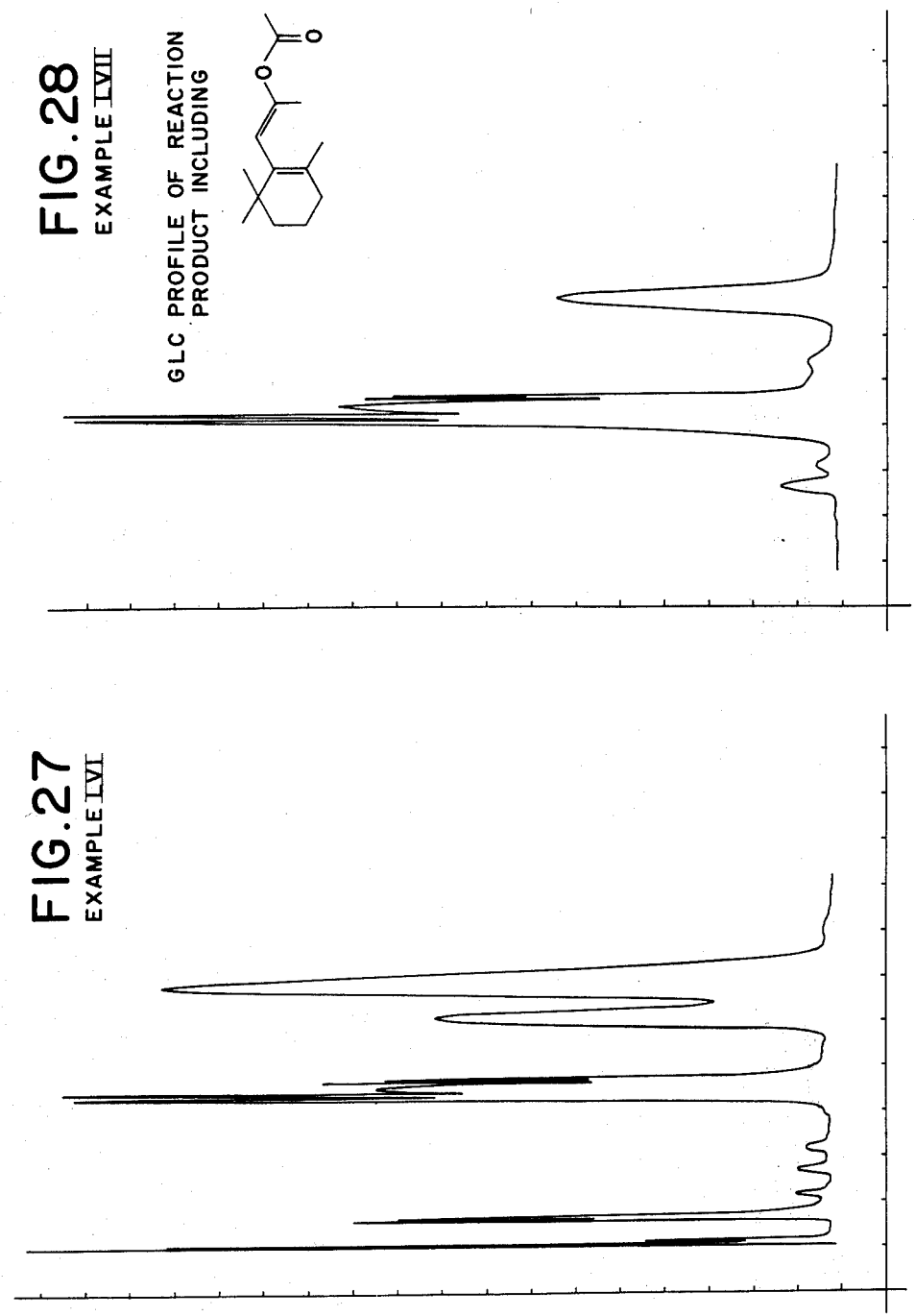

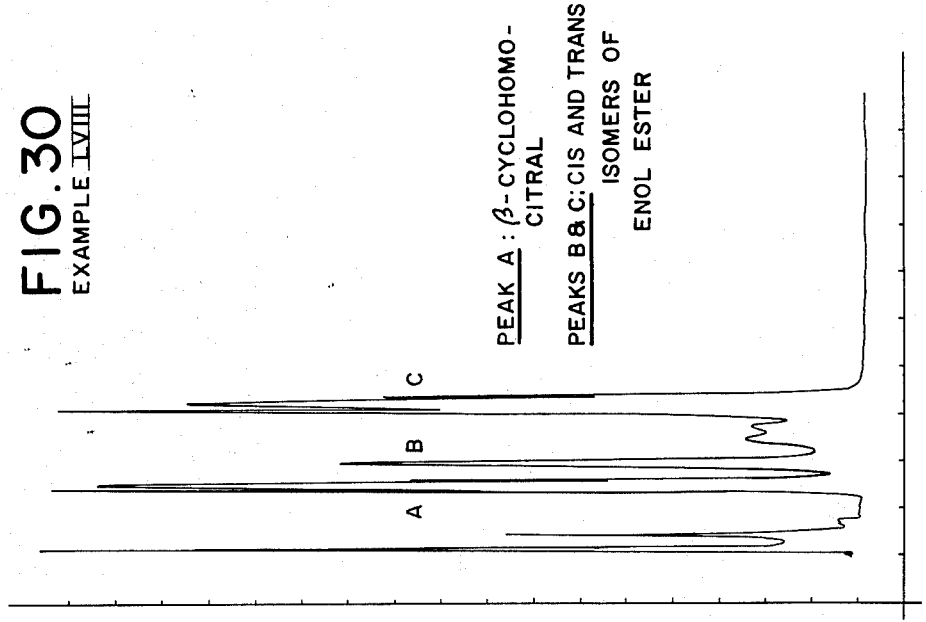
FIG.30 EXAMPLE LVIII
PEAK A: β-CYCLOHOMO-CITRAL
PEAKS B & C: CIS AND TRANS ISOMERS OF ENOL ESTER
PROFILE FOR REACTION PRODUCT CONTAINING CIS-ENOL ACETATE
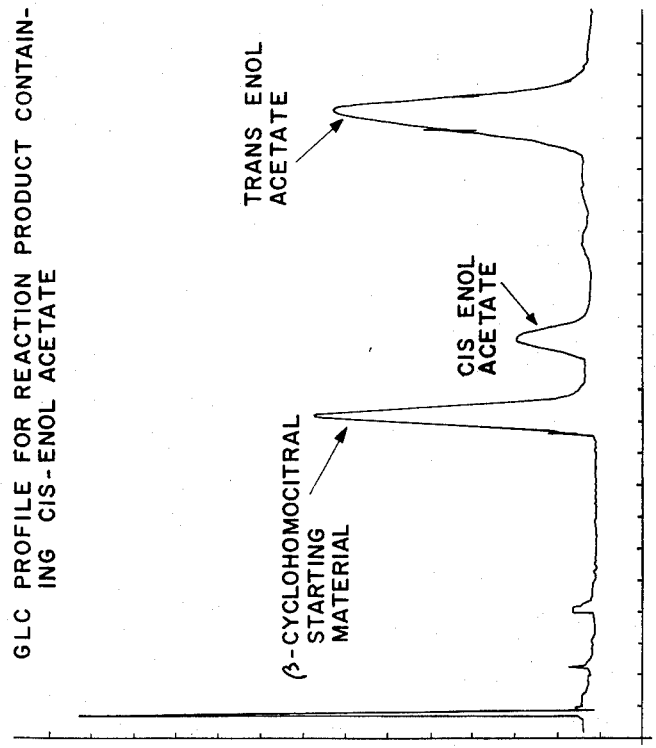
FIG.29 EXAMPLE LVIII
GLC PROFILE FOR REACTION PRODUCT CONTAINING CIS-ENOL ACETATE
β-CYCLOHOMOCITRAL STARTING MATERIAL
CIS ENOL ACETATE
TRANS ENOL ACETATE

EXAMPLE LVIII

NMR SPECTRUM FOR CIS ISOMER OF BETA CYCLOHOMOCITRAL ENOL ACETATE

EXAMPLE XVI

IR SPECTRUM: α-IONONE EPOXIDE

EXAMPLE XVI

EXAMPLE XXV

EXAMPLE LXV

GLC PROFILE:
REACTION PRODUCT

EXAMPLE LXV

GC-MS PROFILE: REACTION PRODUCT

NOVEL ENOL ESTERS

This application is a divisional of application for U.S. Letters Patent Ser. No. 662,820 filed on Mar. 1, 1976, now U.S. Pat. No. 4,000,329 issued on Dec. 28, 1976 which, in turn, is a continuation-in-part of U.S. application for Letters Patent Ser. No. 620,335, filed on Oct. 7, 1975, now U.S. Pat. No. 4,000,090 issued on Dec. 28, 1976 which, in turn, is a continuation-in-part of U.S. application for Letters Patent Ser. No. 507,412, filed on Sept. 19, 1974, (now U.S. Pat. No. 3,940,499 issued on Feb. 24, 1976.

RELATED COMMONLY ASSIGNED PATENT APPLICATIONS AND ISSUED PATENTS

RELATED COMMONLY ASSIGNED PATENT APPLICATIONS AND ISSUED PATENTS

| Serial Number | Filing Date | Status |
|---|---|---|
| 507,414 | 9/19/74 | Pat. No. 3,956,393 |
| 594,100 (c-i-p) | 7/8/75 | Pat. No. 3,980,708 |
| 507,412 | 9/19/74 | Pat. No. 3,940,499 |
| 598,805 (c-i-p) | 7/24/75 | Pat. No. 4,026,824 |
| 598,652 (c-i-p) | 7/24/75 | Pat. No. 4,014,351 |
| 598,654 (c-i-p) | 7/24/75 | Pat. No. 3,959,508 |
| 620,355 (div) | 10/7/75 | Pat. No. 4,000,090 |
| 601,727 | 8/4/75 | Pat. No. 4,028,279 |

BACKGROUND OF THE INVENTION

The present invention relates to enol esters of the genus of alkyl side chain methyl substituted or unsubstituted 2,2,6-trimethyl-1-cyclohexen-1-vinyl alkanoates including (but not limited to) beta-cyclohomocitral enol esters, produced by the novel processes of our invention, and novel compositions using one or more of such enol esters to alter, modify or enhance the flavor and/or aroma of consumable materials or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply and to provide more uniform properties in the finished product.

"Damascenone-like" (damascenone has the structure:

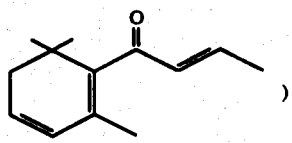

)

sweet, "cocoa-like", dried fruit-like", fruity, apple juice-like, sweet carrot juice, incense-like, ionone-like, spicey, woody, wood resin-like, winey, oriental-/olibanum, clove-like, camphoraceous, rosey, raspberry, raspberry seed, grape, violet-like, caryophyllene-like, and/or floral aromas with fermented tea and tobacco nuances and sweet vegetable, tea, sweet carrot juice, sweet, fruity, dried fruit-like, apple juice, mimosa, raspberry, pear, ionone-like, damascenone-like, rosey, woody, camphoraceous, violet, cedarwood-like, caryophyllene-like, wood resin-like, winey, tobacco-like, hay-like, and raspberry kernel tastes (with sweet aftertastes) are particularly desirable for many uses in foodstuff flavors, chewing gum flavors, toothpaste flavors and medicinal product flavors.

Sweet, fruity, acidic-fruity, dried fruit-like, woody, green, beta-ionone-like notes with animal-tobacco topnotes and cognac, balsamic, tobacco undertones are desirable in several types of perfume compositions, perfumed articles and colognes.

Sweet, woody, floral, fruity, ionone-like, spicey, slightly fatty aromatic aromas prior to smoking and sweet, tobacco-like smoke aroma characteristics in the mainstream on smoking are desirable in tobaccos and in tobacco flavoring compositions.

Archtander, "Perfume and Flavor Chemicals", 1969 discloses the use in perfume compositions and flavors of "cyclocitral", "dehydro-beta-cyclocitral", "isocyclocitral", "alpha-cyclocitrylidene acetaldehyde"and "beta-cyclocitrylidene acetaldehyde", thus:

i. "760 CYCLOCITRAL Alpha-cyclocitral = (2,2,6-trimethyl5-cyclohexen-1-carboxaldehyde).

beta-cyclocitral = (2,2,6-trimethyl- b 6-cyclohexen-1-carboxaldehyde). Both isomers are known and have been produced separately.

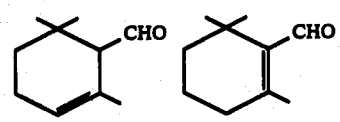

Very rarely offered commercially. These particular cyclocitrals have little or no interest to the creative perfumer, but they have served as part of many pieces of proof that isomers (alpha-beta) do often have different odors."

ii. "761: iso-CYCLOCITRAL A mixture of two chemicals: 3,5,6-trimethyl-3-cyclohexen-1-carboxaldehyde (meta-cyclocitral).

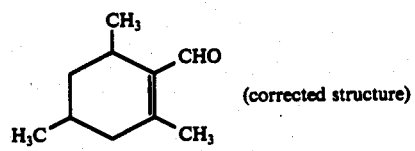

(corrected structure)

2,4,6-trimethyl-4-cyclohexen-1carboxaldehyde (symmetric-iso-cyclocitral).

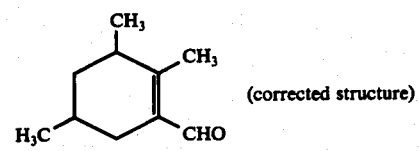

(corrected structure)

Powerful, and diffusive, foliage-green, "dark" weedy and dry odor, sometimes described as "Flower-shop odor". The earthy and wet green notes are quite natural in high dilution and resemble the odor of stems from plants and flowers fresh from the soil.

Finds use in perfume compositions where it blends excellently with Oakmoss products (compensates for sweetness and lifts the topnote), with Ionones(freshness), Geranium and Galbanum (enhances the green and "vegetable" notes ), etc. ..."

iii. "762: alpha CYCLOCITRYLIDENE ACETAL-DEHYDE

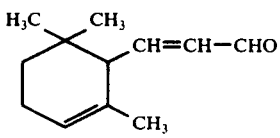

Mild, floral-woody, somewhat oily-herbaceous odor, remotely reminiscent of Rose with similarity to the odor of hydrogenated Ionones.

Suggested for use in perfume compositions. It brings a certain amount of floral lift to Rose compositions, and performs fairly well even in soap. However, the cost of the rarely offered and never readily available lots are rather discouraging to the perfumer, and it is most conceivable that this material can be left out of the perfumer's library without any great loss. ..."

iv. "763: beta-CYCLOCITRYLIDENE ACETAL-DEHYDE 2,6,6-trimethyl-1-cyclohexenyl-beta-acrolein.

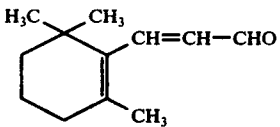

Sweet-woody, rather heavy odor, resembling that of beta-Ionone. More fruity than really floral, but not as tenacious as the Ionone.

Suggested for use in perfume compositions, but since it does not offer any new or unusual odor characteristics, and it cannot be produced in economical competition to betaIonone, there is little or no chance that it will ever become a standard shelf ingredient for the perfumer. ..."

v. "869: DEHYDRO-beta-CYCLOCITRAL (Safranal) 2,6,6-trimethyl-4,4-cyclohexadiene-1-carboxaldehyde

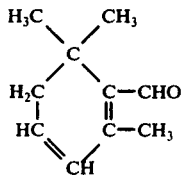

Very powerful, sweet, green-floral and somewhat tobacco-herbaceous odor of good tenacity. In extreme dilution reminiscent of the odor of Safran (Saffron).

Interesting material for fresh topnotes, as a modifier for aldehydic-citrusy notes, as a green-floral topnote in flower fragrances, etc. It blends excellently with the aliphatic Aldehydes, with Oakmoss products and herbaceous oils. ..."

Safranal and beta-cyclocitral are disclosed as volatile constituents of Greek Tobacco by Kimland et al., Phytochemistry 11 (309) 1972. Beta-cyclocitral is disclosed as a component of Burley Tobacco flavor by Demole and Berthet, Helv. Chim. Acta. 55 Fasc 6, 1866 (1972).

Methods for producing enol esters are disclosed in the prior art. Thus, for example, heptaldehyde enol acetate is disclosed to be produced according to the process of reacting heptaldehyde with acetic anhydride in the presence of crystalline potassium acetate at reflux temperatures of 155°–160° C by Bedoukian, J.Am.Chem.-Soc. 66, August, 1944, pages 1325–1327.

However, no disclosures exist in the prior art indicating the existence or implying the organoleptic uses of enol esters related to those of the instant invention or methods for synthesizing such compounds.

BRIEF DESCRIPTION OF THE DRAWINGS

FIG. 3 is the NMR spectrum for the cis isomer of beta-cyclohomocitral enol butyrate produced according to Example XXXIV.

FIG. 4 is the IR spectrum for the cis isomer of beta-cyclohomocitral enol butyrate produced according to Example XXXIV.

FIG. 21 is the GLC profile for the reaction product of Example L wherein beta-cyclohomocitral enol acetate is produced.

FIG. 22 is the GLC profile for the reaction product of Example LI wherein beta-ionone epoxide is produced.

FIG. 23 is the GLC profile for the reaction product of Example LII.

FIG. 24 is the GLC profile for the reaction product of Example LIII wherein beta-cyclohomocitral enol acetate is produced.

FIG. 27 is the GLC profile for the reaction product of Example LVI wherein beta-cyclohomocitral enol acetate is produced.

FIG. 28 is the GLC profile for the reaction product of Example LVII wherein the enol acetate having the structure:

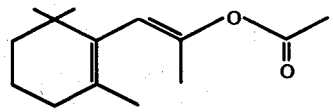

is produced.

FIG. 29 is the GLC profile for the reaction product of acetic anhydride and beta-cyclohomocitral produced according to Example LVIII.

FIG. 30 is the GC-MS profile for the reaction product produced according to Example LVIII.

Figure 31:
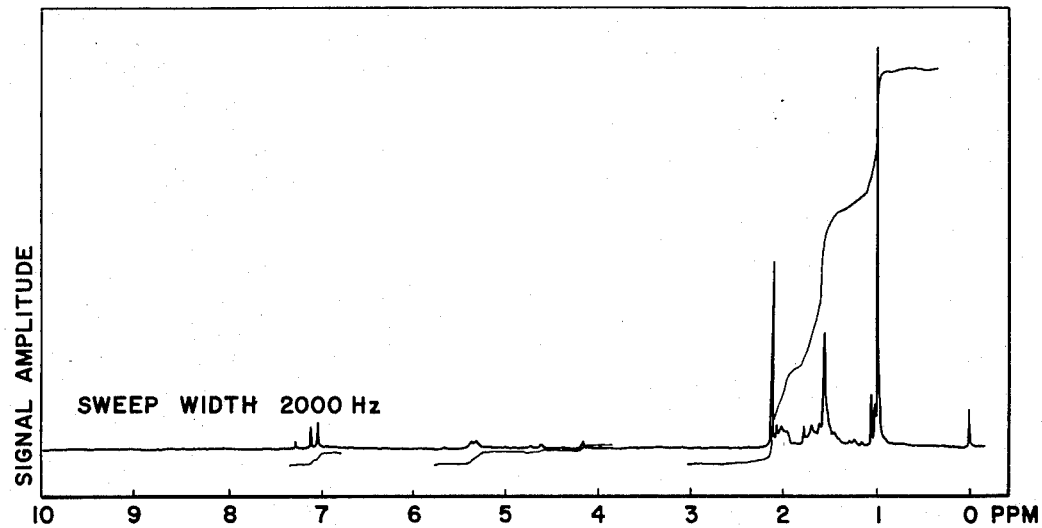

FIG. 31 is the NMR spectrum for the beta-cyclohomocitral cis enol acetate produced according to Example LVIII.

Figure 32:
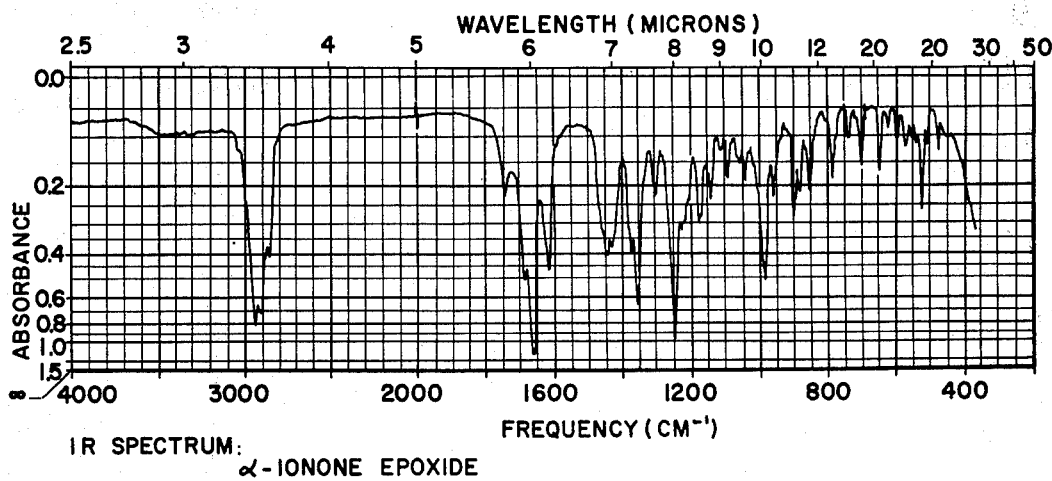

FIG. 32 is the Infrared spectrum of alpha-ionone epoxide produced in Example XVI.

Figure 33:
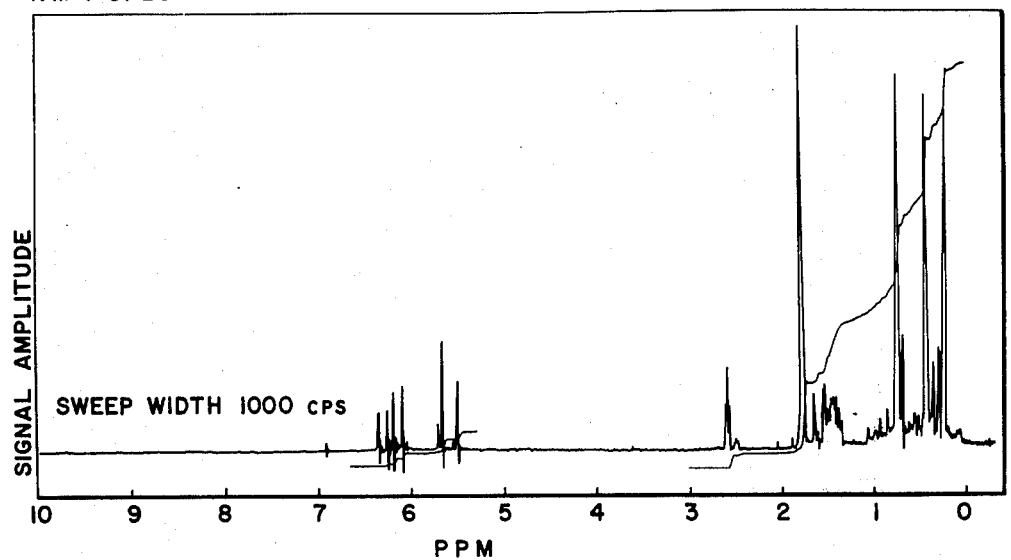

FIG. 33 is the NMR spectrum for alpha-ionone epoxide produced in Example XVI.

Figure 34:
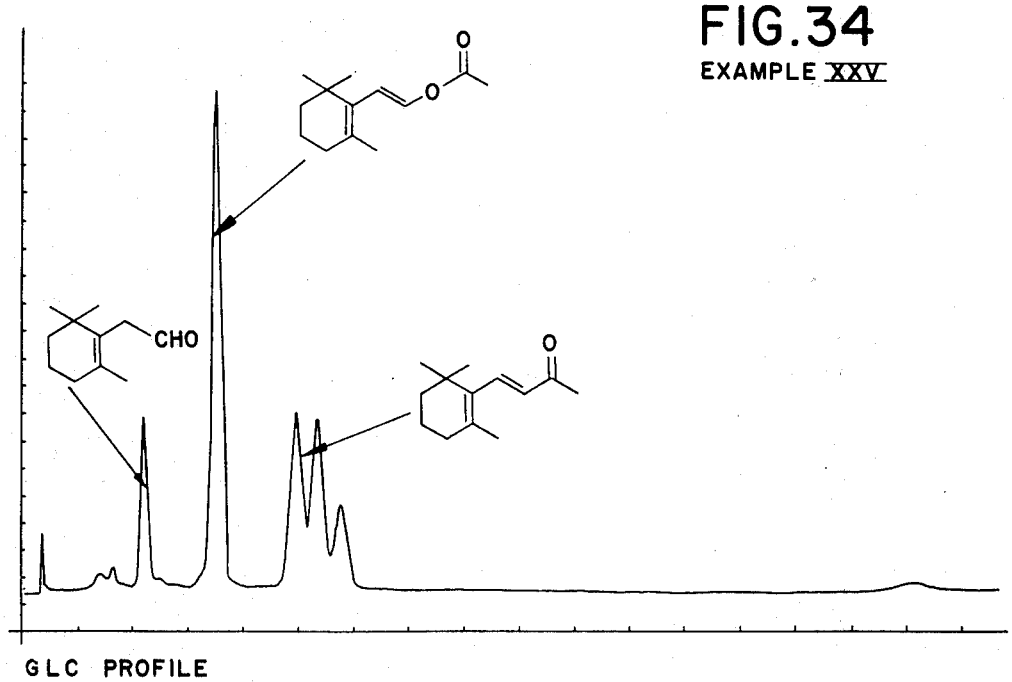

FIG. 34 is the GLC profile of the reaction product produced according to Example XXV, containing beta-cyclohomocitral enol acetate.

Figure 35:
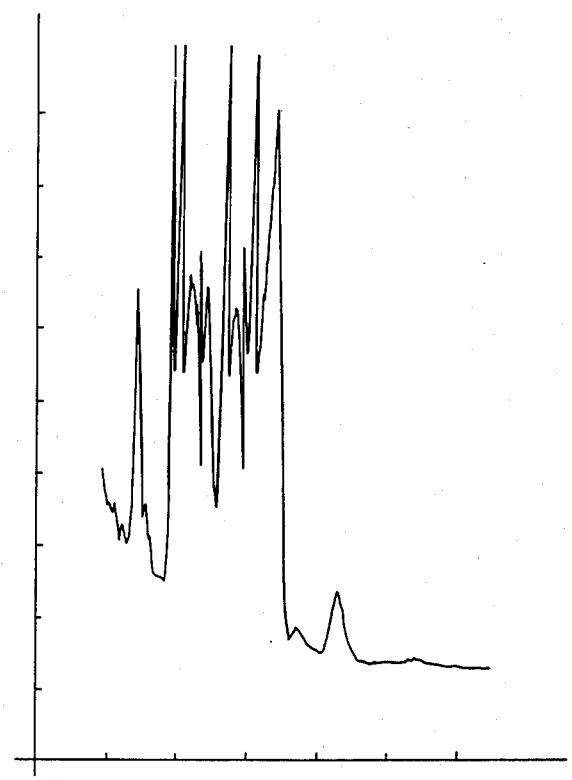

FIG. 35 is the GLC profile of the reaction product produced according to Example LXV, containing beta-cyclohomocitral enol laurate.

Figure 36:
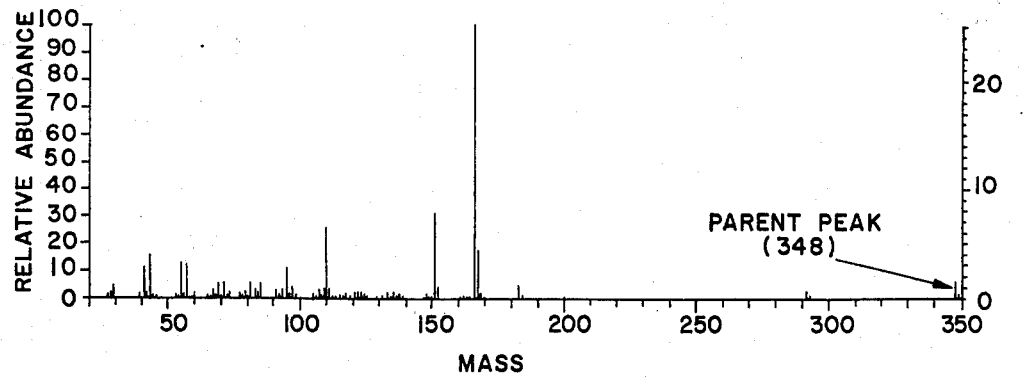

FIG. 36 is the GC-MS profile of the reaction product produced according to Example LXV, containing beta-cyclohomocitral enol laurate.

THE INVENTION

It has now been discovered that novel solid and liquid foodstuff, chewing gum, medicinal product and toothpaste compositions and flavoring compositions therefor having damascenone-like (damascenone has the structure:

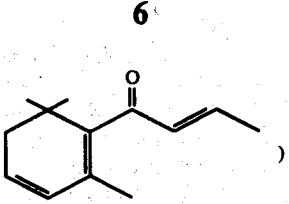

sweet, cocoa-like, dried fruit-like, fruity, apple juice-like, sweet carrot juice, incense-like, ionone-like, spicey, woody, wood resin-like, winey, oriental/olibanum, clove-like, camphoraceous, rosey, raspberry, raspberry seed, grape, violet-like, caryophyllene-like, and/or floral aromas with fermented tea and tobacco nuances and sweet vegetable, tea, sweet carrot juice, sweet, fruity, dried fruit-like, apple juice, mimosa, raspberry, pear, ionone-like, damascenone-like, rosey, woody, camphoraceous, violet, cedarwood-like, caryophyllene-like, wood resin-like, winey, tobacco-like, hay-like and/or raspberry kernel tastes with sweet aftertastes; novel perfume compositions, colognes and perfumed articles having sweet, fruity, acidic-fruity, dried fruit-like, woody, green, beta-ionone-like notes with animal-tobacco topnotes and cognac, balsamic, tobacco undertones; as well as novel tobacco and tobacco flavoring compositions having sweet, woody, floral, fruity, ionone-like, spicey, slightly fatty aromatic aromas prior to smoking and sweet, tobacco-like smoke aroma characteristics in the mainstream on smoking, may be provided by the utilization of one or more enol esters (either the "cis" or the "trans" isomer or a mixture of cis and trans isomers) having the formula:

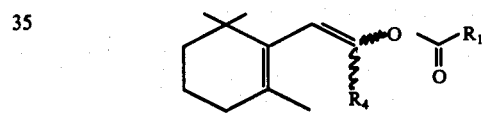

(wherein $R_4$ is hydrogen or methyl and $R_1$ is one of $C_1$-$C_{11}$ alkyl) in foodstuffs, chewing gums, toothpastes, medicinal products, perfume compositions, perfumed articles, colognes and tobaccos as well as tobacco substitutes.

The enol esters useful as indicated supra may be produced, preferably, by one of several processes.

A first process comprises an oxidation reaction of beta-ionone or a higher alkyl homologue of beta-ionone with either performic acid, peracetic acid, perpropionic acid or m-chloroperbenzoic acid to form an enol ester.

More specifically, this process comprises the step of reacting beta-ionone or a higher alkyl homologue thereof having the formula:

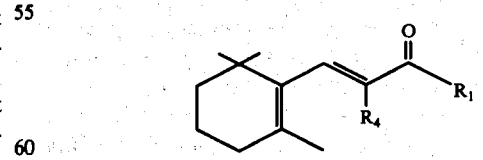

with a peracid having the formula:

(wherein $R_1$ is one of $C_1$-$C_{11}$ alkyl, $R_4$ is hydrogen or methyl and $R_2$ is one of hydrogen, ethyl, methyl or m-chlorophenyl) in the absence of substantial quantities of solvents which are reactive with one of the reactants (e.g. the peracid) such as N,N-dimethyl aniline, and, in addition, in the case where a buffer is not present, in the absence of substantial quantities of the solvent, dimethyl formamide; and, in the presence of one or more of the following solvents:

Methylene chloride;
Acetic acid;
Formic acid;
Propionic acid;
Benzene;
Cyclohexane;
Formamide; and
Chloroform to form primarily the trans isomer of the enol ester having the formula:

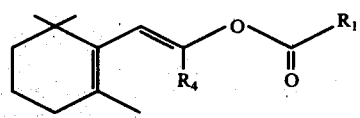

and not the expected epoxide having one of the formulae:

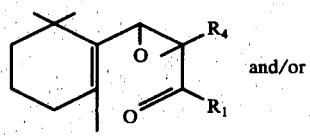
and/or

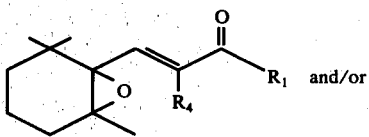
and/or

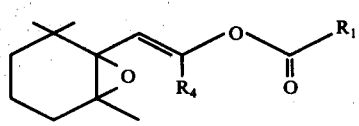

(As to the latter structure wherein $R_4$ is hydrogen and $R_1$ is methyl, see S. Isoe, et al, Tetrahedron Letters, No. 53, 5561-4 (1968)).

This reaction is preferably carried out in the presence of a buffer such as an alkali metal salt of a lower alkanoic acid or an alkali metal carbonate and in the presence of a lower alkanoic acid such as propionic acid, acetic acid or formic acid with the following provisos:

i. The reaction is preferably carried out at temperatures of from − 10° C up to about 75° C. Lower temperatures result in less complete reaction and, in some cases, cause the reaction mass to freeze, and temperatures higher than 75° C result in lower yields of the desired product and significantly higher percentages of by-products. The most preferred temperature range for the reaction is −5° to 30° C;

ii. A slight molar excess (from 10 up to 15 percent) of peracid gives a slightly higher yield of product. A large excess (about 200 percent), however, results in the formation of dihydroactinodiolide having the structure:

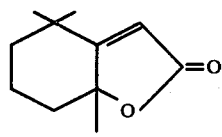

in about 30–35 percent yield when no buffer (e.g., potassium acetate) is present in the reaction mass;

iii. Where potassium carbonate is substituted for potassium acetate as a buffer, the yield of product obtained is substantially the same;

iv. On the other hand, a slightly lower yield of product is obtained by substituting sodium acetate for potassium acetate as the buffer;

v. Substitution of formic acid for acetic acid in the reaction mass gives rise to a lower yield of product;

vi. Omission of the buffer (i.e., thus performing the reaction under strongly acidic conditions) results in an incomplete reaction, lower yield and greater quantity of by-product(s) and insignificant or no yield of enol ester when dimethyl formamide is used as the solvent;

vii. The use of dimethyl formamide as solvent when no buffer such as sodium acetate is used results in essentially the exclusive but very slow formation of beta-ionone epoxide having the structure:

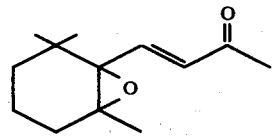

in greater than 70% yield and, accordingly, in the absence of buffer, substantial quantities of dimethyl formamide must be avoided; and viii. The use of monoperphthalic acid (formed in situ from phthalic anhydride and hydrogen peroxide) yields beta-ionone epoxide in 60–70 percent yield;

ix. Whereas m-chloroperbenzoic acid is useful in producing the enol esters of our invention, the use of perbenzoic acid in place of a peralkanoic acid, or m-chloroperbenzoic acid gives rise to the production of beta-ionone epoxide. See R. Yves, et al, Helv. Chim. Acta, 29, 880 (1946). Indeed, when using 2 moles of perbenzoic acid, the corresponding epoxy enol acetate is formed virtually quantitatively; (See S. Isoe, et al, Tetrahedron Letters, No. 53, 5561 (1968)); and x. The use of permaleic acid yields beta-ionone epoxide and only traces of the desired enol acetate.

Thus, a specific conclusion that may be properly reached is that a peralkanoic acid such as peracetic acid or m-chloroperbenzoic acid in slight excess in the presence of a buffer system, preferably composed of acetic acid/potassium acetate is a preferred method to oxidize beta-ionone or higher alkyl homologue thereof at from about −5° C to about 30° C to the corresponding enol acetate.

The resulting reaction product, the enol acetate (primarily the trans isomer) may then be refined according to standard techniques, e.g., preparative gas chromatography, extraction, distillation and the like as further exemplified herein; or it may be further reacted via an ester interchange reaction to form other enol esters thereby carrying out a second process of our invention.

The first process is specific to beta-ionone and adjacent higher alkyl homologues thereof having the structure:

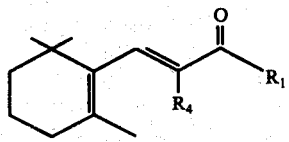

wherein $R_1$ is $C_1$-$C_{11}$ alkyl and $R_4$ is hydrogen or methyl. As further exemplified infra, when the reaction conditions of this process are applied to alpha-ionone, as opposed to beta-ionone or its higher alkyl homologues, epoxide formation occurs and, at best, a small amount of enol ester is formed.

A second process comprises reacting beta-cyclohomocitral enol acetate or a higher methyl homologue thereof formed in the first process (set forth supra) with an alkanoic acid anhydride in the presence of a paratoluene sulfonic acid or alkali metal acetate (e.g., sodium or potassium acetate) catalyst to form a second enol ester (a mixture of cis and trans isomers) according to the reaction:

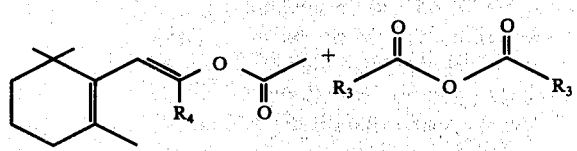

wherein M is an alkali metal such as Na and K and wherein $R_3$ is $C_2$-$C_{11}$ alkyl such as ethyl, n-propyl, isopropyl, 1-butyl, 2-butyl, 2-methyl-1-propyl, 2-methyl-2-propyl, n-heptyl, n-octyl or n-undecyl and $R_4$ is hydrogen or methyl. This reaction is carried out at elevated temperatures (100° to 200° C) over a period of from 3 hours up to 10 hours depending upon the concentration of paratoluene sulfonic acid catalyst or alkali metal acetate catalyst. It is preferable that the mole ratio of alkanoic acid anhydride:enol acetate be greater than 1 and preferably 1.5:1 because of the necessity to completely react the much more costly enol acetate. The mole ratio of enol acetate:paratoluene sulfonic acid catalyst or alkali metal acetate catalyst is preferably from 1:0.01 up to 1:0.5 with the most convenient ratio being 1:0.01.

A third process whereby mixtures of cis and trans isomers are formed involves the reaction of beta-cyclohomocitral itself with an alkanoic acid anhydride or an acyl halide in the presence of either an alkali metal acetate base or a catalytic quantity of paratoluene sulfonic acid according to one of the following reaction sequences:

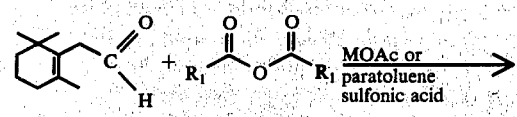

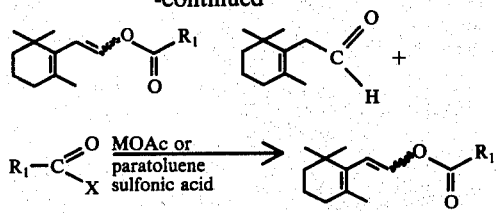

wherein X is chloro or bromo and wherein $R_1$ is $C_1$-$C_{11}$ alkyl such as methyl, ethyl, n-propyl, isopropyl, 1-butyl, 2-butyl, 2-methyl-1-propyl, 2-methyl-2-propyl, 1-pentyl, 2-pentyl, 3-pentyl, 2-methyl-1-butyl, 2-methyl-2-butyl, 2-methyl-3-butyl, 1-heptyl, 1-octyl, 2-methyl-1-nonyl and 1-undecyl and M is alkali metal such as sodium and potassium. The reaction is carried out at elevated temperatures (25°-175° C) preferably in the absence of any solvent. In all cases, it is preferred that the alkanoic acid anhydride (or acyl halide) be in molar excess with respect to the beta-cyclohomocitral. It is preferred that the mole ratio of alkanoic acid anhydride:beta-cyclohomocitral be 1.5:1. When using acyl halide it is preferred that the ratio of acyl halide:beta-cyclohomocitral be about 1:1.5 up to 1:2.0. Ratios outside of the foregoing limits are workable, however, when using such ratios, less economical and steps of greater complexity are required. When the reaction is carried out in the presence of an alkali metal acetate it is preferred that the mole ratio of alkali metal acetate:-beta-cyclohomocitral be about 0.1:1. When the reaction is carried out in the presence of alkali metal acetate, it is performed at elevated temperatures (100°-200° C) for a period of from 3 up to 10 hours. When the reaction is carried out using a paratoluene sulfonic acid catalyst it is preferred that the mole ratio of beta-cyclohomocitral:paratoluene sulfonic acid be from 1:0.01 up to 1:0.1 with the most convenient mole ratio being 1:0.02. When using paratoluene sulfonic acid catalyst the reaction is carried out at reflux for a period of time from 10 up to 40 hours depending upon the process economics and desired yield.

One or more of the enol esters of our invention is capable of supplying and/or potentiating certain flavor and aroma notes usually lacking in many fruit flavors (e.g. berry, including raspberry; grape and apple juice) clove flavors, cinnamon flavors, tea flavors, honey flavors, dried fruit flavors, wine flavors and cocoa flavors as well as tobacco flavors heretofore provided. Furthermore, the beta-cyclohomocitral enol esters of our invention are capable of supplying certain fragrance notes usually lacking in many perfumery materials, for example, rose fragrances. The following Table I sets forth organoleptic properties of specific enol esters of our invention:

TABLE I

| NAME OF COMPOUND | STRUCTURE | FLAVOR PROPERTIES | PERFUMERY PROPERTIES |
|---|---|---|---|
| trans beta-cyclo-homocitral enol acetate | 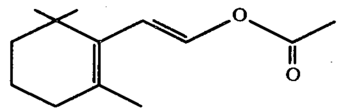 | Sweet, fruity, raspberry, ionone, rosey, raspberry seed aroma character with a sweet, fruity, raspberry, ionone, woody, raspberry/kernel flavor character and a sweet aftertaste at 5 ppm. | At 10% in food grade ethyl alcohol, a floral, minty aroma with beta-ionone type, violet and rosey nuances; and in addition, woody type notes seen in natural vetivert. |
| cis beta-cyclo-homocitral enol acetate | 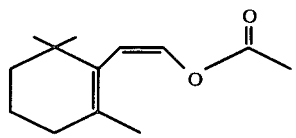 | A sweet, floral, ionone-like, woody, violet, fruity, cary-ophyllene aroma with hay-like, ionone-like, woody, violet, caryophyllene-like, tobacco and cedarwood-like flavor characteristics at 5 ppm. | Earthy, camphoraceous and sea-like aroma with ionone and fruity nuances in addition to sweet, beta-ionone-like, tobacco and fruity nuances. |
| cis beta-cyclo-homocitral enol butyrate | 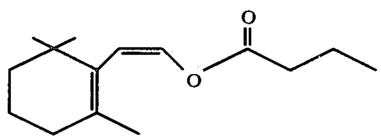 | Sweet, fruity, damascenone-like, incense-like, woody, floral, ionone-like aroma characteristics with sweet, fruity, tea-like, hay-like, ionone-like, raspberry, pear, dried fruit, astringent flavor characteristics at 30 ppm. At 4 ppm the aroma notes are not as delicate as those of the trans isomer and the ionone notes are dominating. At 20 ppm and 50 ppm woody/ionone-like notes start appearing. | Dried fruit-like, sweet, damascone-like, ionone-like aroma with fruity nuances. |
| trans beta,cyclo-homocitral enol butyrate | 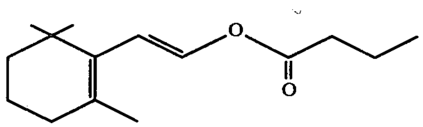 | Sweet, damascenone-like, fruity, rosey, winey, apple juice-like, tea, tobacco aroma character-istics and sweet, fruity, damascenone, raspberry, apple juice, rosey, winey and astringent flavor notes at 30 ppm. At 4 ppm has the delicate aroma notes of beta-cyclohomocitral with the taste also as delicate as the aroma. At 10 ppm has the aroma of delicate rose buds with raspberry, fruity nuances and apple and wine topnotes with sweet, fruity, winey, lavender flavor notes. | Sweet, fruity, ionone-like, tobacco, damascenone-like aroma with a sweaty undertone. |
| trans beta,cyclo-homocitral enol isobutyrate | 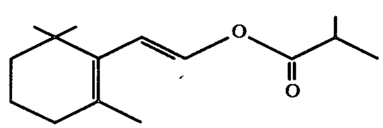 | A sweet, woody, rosey, fruity, wood rosin-like, spicey, apple juice-like aroma character with a fruity, apple, rasp-berry, woody, wood rosin, tea, astringent flavor character at 5 ppm. | Acidic, fruity, damascone-like with more animal/tobacco nuances than cis isomer; also more aesthetic than cis isomer. |

TABLE I-continued

| NAME OF COMPOUND | STRUCTURE | FLAVOR PROPERTIES | PERFUMERY PROPERTIES |
|---|---|---|---|
| cis beta-cyclo-homocitral enol isobutyrate | 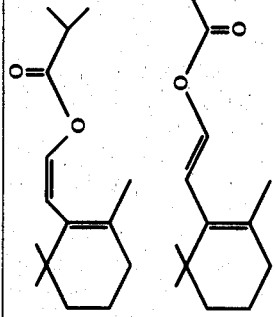 | Sweet, oriental/olibanum, delicate rosey, fruity, ionone-like, clove, camphoraceous aroma characteristics with rosey, woody, clove, mimosa, ionone-like, musty and camphoraceous flavor character at 5 ppm. | Sweet, woody, green, tobacco aroma with fruity and resinous notes; not quite as fruity as the trans isomer, also has ionone and mimosa nuances. |
| trans beta-cyclo-homocitral enol octanoate | 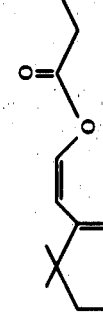 | Ionone and woody aroma characteristics with ionone, woody, musty and astringent flavor notes at 5 ppm. | Woody, cheesy and fatty aroma with warm, fruity notes and a cognac, balsamic and tobacco undertone; warm and fruity notes more intense than in cis isomer. |
| cis beta-cyclo-homocitral enol octanoate | 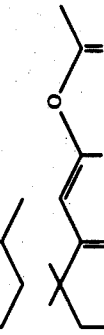 | Sweet, rosey, damascenone-like, dried fruit and cocoa aroma characteristics with sweet, delicate rosey, damascenone-like, tea, apple juice-like, tobacco flavor character at 15 ppm. | Woody, cheesy and fatty aroma with ionone nuance. |
| trans alpha 2,6,6-tetramethyl-1-cyclohexene-1-ethenol acetate | 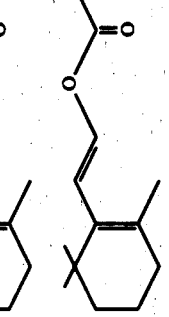 | Woody, ionone, gasoline-like, tomato character with woody, ionone-like, gasoline-like and solvent-like flavor character at 1 ppm. | Oily, woody, musky, butyric, ionone aroma with woody and burnt notes on dry out; not as sweet or fruity or berry-like as beta-cyclohomocitral enol acetate. |
| trans beta-cyclo-homocitral enol propionate | 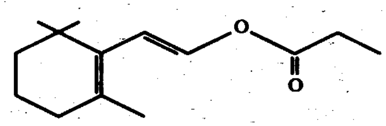 | Sweet, floral, ionone-like, raspberry, dried fruit and tobacco aroma character with sweet, fruity, ionone-like, raspberry, dried fruit, tobacco flavor character at 1 ppm; about 2 times as strong and is sweeter, fruitier and more raspberry-like than trans beta-cyclohomocitral enol acetate. | A butyric/propionic acid top-note with tobacco, woody and ionone notes; not as pleasant as beta-cyclohomocitral enol acetate. |

When the enol esters of our invention are used as food flavor adjuvants, the nature of the co-ingredients included with each of the said enol esters in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, diary products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates one or more of the enol esters of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectines, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta,-beta-dimethylacrolein, methyl-n-amyl ketone, n-hexenal, 2-hexenal, isopentanal, hydrocinnamic aldehyde, cis-2-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutylrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as γ-nonalactone; sulfides, e.g., methyl sulfide and other materials such as maltol, acetoin and acetals (e.g., 1,1-diethoxy-ethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the enol ester or esters of our invention by not covering or spoiling the organoleptic properties (aroma and/or taste) thereof; (ii) be nonreactive with the enol ester or esters of our invention and (iii) be capable of providing an environment in which the enol ester or esters can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of enol esters or esters employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of enol ester or esters will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, with respect to ultimate food compositions, chewing gum compositions, medicinal product compositions and toothpaste compositions, it is found that quantities of enol ester or esters ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein the enol ester or esters is added to the foodstuff as an integral component of a flavoring composition, it is, of course, essential that the total quantity of flavoring composition employed by sufficient to yield an effective enol ester concentration in the foodstuff product.

Food flavoring compositions prepared in accordance with the present invention preferably contain the enol ester or esters in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the enol ester or esters with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, subgar and the like and enol ester or esters in a dry blender until the requisite degree of uniformity is achieved.

It is presently preferred to combine with the enol ester or esters of our invention, the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole
2,3-Dimethyl pyrazine;

2-Ethyl-3-methyl pyrazine;
3-Phenyl-4-pentenal
2-Phenyl-2-hexenal;
2-Phenyl-2-pentenal;
3-Phenyl-4-pentenal diethyl acetal;
Damascone (1-crotonyl-2,2,6-trimethylcyclohex-1-one)
Damascenone (1-crotonyl-2,2,6-trimethylcyclohexa-1,5-diene)
Beta-cyclohomocitral (2,2,6-trimethyl-cyclohex-1-ene carboxaldehyde)
Isoamyl butyrate;
Cis-3-hexenol-1;
2-Methyl-2-pentenoic acid;
Elemecine (4-allyl-2,2,6-trimethoxy benzene);
Isoelemecine (4-propenyl-1,2,6-trimethoxy benzene); and
2-(4-Hydroxy-4-methylpentyl) norborandiene prepared according to U.S. application for Letters Patent Ser. No. 461,703, filed on Apr. 17, 1974

An additional aspect of our invention provides an organoleptically improved smoking tobacco product and additives therefor, as well as methods of making the same which overcome specific problems heretofore encountered in which specific desired sweet, floral, woody, spicey, ionone-like and fruity flavor characteristics of natural tobacco (prior to smoking and on smoking; in the mainstream and in the sidestream) are created or enhanced or modified or augmented and may be readily controlled and maintained at the desired uniform level regardless of variations in the tobacco components of the blend.

This invention further provides improved tobacco additives and methods whereby various desirable natural aromatic tobacco flavoring characteristics with sweet, floral and fruity notes may be imparted to smoking tobacco products and may be readily varied and controlled to produce the desired uniform flavoring characteristics.

In carying out this aspect of our invention, we add to smoking tobacco materials or a suitable substitute therefor (e.g., dried lettuce leaves) an aroma and flavor additive containing as an active ingredient one or more enol esters of our invention.

In addition to the enol or esters of our invention other flavoring and aroma additives may be added to the smoking tobacco material or substitute therefor either separately or in mixture with the enol ester or esters as follows:

I. Synthetic Materials:

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate
2-Hexenol-1,2-methyl-5-isopropyl-1,3-nonadiene-8-one;
2,6-Dimethyl-2,6-undecadiene-10-one;
2-Methyl-5-isopropyl acetophenone;
2-Hydroxy-2,4,4,8a-tetramethyl-1(2-hydroxyethyl)-decahydronaphthalene;
Dodecahydro-3a,6,6,9a-tetramethylnaphtho-(2,1-b)-furan
4-Hydroxy hexanoic acid, gamma lactone; and
Polyisoprenoid hydrocarbons defined in Example V of U.S. Patent 3,589,372 issued on June 29, 1971.

II. Natural Oils

Celery seed oil;
Coffee extract;
Bergamot Oil;
Cocoa extract;
Nutmeg oil; and
Origanum oil.

An aroma and flavoring concentrate containing beta-cyclohemocitral enol ester or esters and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and-/or sweet notes, we have found that satisfactory results are obtained if the proportion by weight of the sum total of enol ester or esters to smoking tobacco material is between 250 ppm and 1,500 ppm (.025%-.15%) of the active ingredients to the smoking tobacco material. We have further found that satisfactory results are obtained if the proportion by weight of the sum total of enol ester or esters used to flavoring material is between 2,500 and 15,000 ppm (0.25%-1.5%).

Any convenient method for incorporating the enol ester (or esters) into the tobacco product may be employed. Thus, the enol ester (or esters) taken alone or along with other flavoring additives may be dissolved in a suitable solvent such as ethanol, diethyl ether and/or volatile organic solvents and the resulting solution may either be spread on the cured, cased and blended tobacco material or the tobacco material may be dipped into such solution. Under certain circumstances, a solution of the enol ester (or esters) taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the enol ester (or esters) in excess of the amounts or concentrations above indicated so that when blended with other tobaccos, the final product will have the percentage within the indicated range.

In accordance with one specific example of our invention, an aged, cured and shredded domestic burley tobacco is spread with a 20% ethyl alcohol solution of beta-cyclohomocitral enol acetate having the structure:

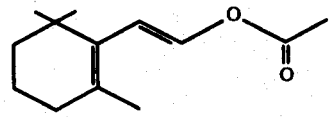

in an amount to provide a tobacco composition containing 800 ppm by weight of beta-cyclohomocitral enol acetate on a dry basis. Thereafter, the alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as being sweeter, more aromatic, more tobacco-like and having sweet, fruity notes.

While our invention is particularly useful in the manufacture of smoking tobacco, such as cigarette tobacco, cigar tobacco and pipe tobacco, other tobacco products formed from sheeted tobacco dust or fines may also be used. Likewise, the enol ester (or esters) of our invention can be incorporated with materials such as filter tip materials, seam past, packaging materials and the like which are used along with tobacco to form a product adapted for smoking. Furthermore, the enol ester (or mixture of esters) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The enol ester (or mixture of esters) and one or more auxiliary perfume ingredients, including, for example, alcohols, aldehydes, nitriles, esters, cyclic esters, and natural essential oils, may be admixed so that the combined odors of the individual components produce a pleasant and desired fragrance, particularly and preferably in rose fragrances. Such perfume compositions usually contain (a) the main note or the "bouquet" or foundation stone of the composition, (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect to the perfume composition will be at least the sum total of the effects of each of the ingredients. Thus, one or more of the enol esters can be used to alter, modify or enhance the aroma characteristics of a perfume composition, for example, by utilizing or moderating the olfactory reaction contributed by another ingredient in the composition.

The amount of enol ester (or mixture of esters) of our invention which will be effective in perfume compositions as well as in perfumed articles and colognes depends on many factors, including the other ingredients, their amounts and the effects which are desired. It has been found that perfume compositions containing as little as 0.01% of enol ester (or mixture of esters) or even less (e.g., 0.005%) can be used to impart a sweet, floral, fruity odor with beta-ionone-like and tobacco-like nuances to soaps, cosmetics or other products. The amount employed can range up to 70% of the fragrance components and will depend on considerations of cost, nature of the end product, the effect desired on the finished product and the particular fragrance sought.

The enol esters (or mixtures of esters) of our invention are useful [taken alone or together with other ingredients in perfume compositions] as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of enol ester (or mixture of esters) will suffice to impart an intense floral note to rose formulations. Generally, no more than 3% of enol ester (or mixture of esters) based on the ultimate end product, is required in the perfume composition.

In addition, the perfume composition or fragrance composition of our invention can contain a vehicle, or carrier for the enol ester or mixture of enol esters. The vehicle can be a liquid such as an alcohol, a non-toxic alcohol, a non-toxic glycol, or the like. The carrier can also be an absorbent solid, such as gum (e.g., gum arabic) or components for encapsulating the composition (such as gelatin).

It will thus be apparent that the enol ester (or the mixture of esters) of our invention can be utilized to alter, modify or enhance sensory properties, particularly organoleptic properties, such as flavor(s) and/or fragrance(s) of a wide variety of consumable materials.

Examples I-VIII, X, XVII, XXV, XXVI, XXXVII, XXXVIII, XLVIII, XLIX, L, LIII-LVIII, LX-LXIV and LXX, following, serve to illustrate processes for specifically producing the enol esters useful in our invention.

Examples IX and LIX, following, serve to illustrate the unworkability of one of these processes where dimethyl formamide, in the absence of an inorganic buffer, is used in the oxidation reaction of beta-ionone with peracetic acid. Example III serves to illustrate the unworkability of that reaction where no buffer, e.g., sodium acetate, is used. Example LI shows the unworkability of the above process using a perphthalic acid anhydride oxidizing agent. Example LII illustrates the unworkability of the above process when using a dimethyl aniline solvent in which the dimethyl aniline is oxidized preferentially over the beta-ionone.

Examples XI-XV, XVIII-XXIV, XXVII-XXXII, XXXIX-XLVI and LXVI-LXIX illustrate the utilities of the enol esters of our invention.

Example XVI illustrates the unworkability of the above process in forming an alpha-ionone enol ester when operated on alpha-ionone rather than beta-ionone.

Example XLVII illustrates the unworkability of permaleic acid.

It will be understood that these Examples are illustrative and the invention is to be considered restricted thereto only as indicated in the appended claims.

All parts and percentages given herein are by weight unless otherwise specified.

EXAMPLE I

PRODUCTION OF TRANS BETA-CYCLOHOMOCITRAL ENOL ACETATE FROM BETA-IONONE

Into a two liter reaction flask equipped with stirrer, thermometer, reflux condenser, addition funnel and cooling bath, the following material are added:

i. Solution of 96 grams beta-ionone in 300 cc chloroform; and

II. 30 grams sodium acetate

95 Grams of 40% peracetic acid is then added, with cooling, slowly at 10° C during a period of one hour. The reaction mass is stirred at 10° C for an additional hour and the solution is then allowed to slowly warm up to room temperature. The reaction mass is then poured into one liter of water and the resultant organic and aqueous phases are separated. The aqueous phase is then extracted with 100 cc of chloroform and the resultant organic phases are then bulked. The solvent is evaporated from the organic phase to yield 99.5 grams of an oil which is then chromatographed on 1,000 grams of alumina deactivated with 5% W/W water and eluted as follows:

| Fraction | Volume of Solvent | Quantity of Solute Eluted |
|---|---|---|
| 1 | 750 cc hexane | 8.0 grams |
| 2 | 500 cc hxane | 31.7 grams |
| 3 | 300 cc hexane | 13.5 grams |
| 4 | 250 cc hexane | 7.0 grams |
| 5 | 250 cc hexane | 1.9 grams |
| 6 | 250 cc hexane | 1.6 grams |
| 7 | 600 cc 25% diethyl ether-75% hexane | 15.6 grams |
| 8 | 600 cc diethyl ether | 15.3 grams |

Fractions 1–4 are composed mainly of trans beta-cyclohomocitral enol acetate.

The spectral data for a purified sample of this material obtained by preparative gas chromatography confirm the structure:

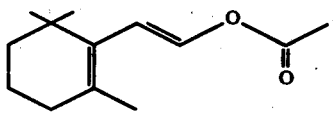

The mass spectrum of this compound has the following fragmentation pattern, in decreasing order of ion abundance: m/e 166 (100), 151 (81), 43 (30), 208 (30) (molecular ion) and 95 (18). The infrared spectrum shows the following characteristic absorption bands (cm$^{-1}$):

| | |
|---|---|
| 3090 | H<br>/<br>C=C (C—H)<br>/<br>H |
| 1752 | C=O (vinyl ester) |
| 1650 | C=C (conjugated with oxygen) |
| 1360 | CH$_3$ |
| 1380 | \C/ |
| | /<br>CH$_3$ |
| 1365 | —CH$_3$ |
| 1215 | |
| 1080 | C—O (of the ester) |
| 930 | 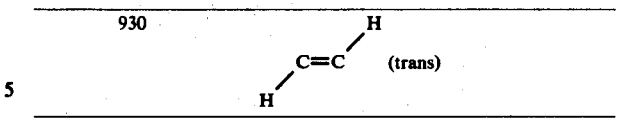 |

The NMR spectrum exhibits in CDCl$_3$ solution the following proton absorptions (chemical shifts in ppm):

| Ppm | Multiplicity | Assignment | No. of Protons |
|---|---|---|---|
| 1.00 | (s) | CH$_3$\ /CH$_3$<br>C | 6H |
| 1.70–1.40 | (m) | $(CH_2)_2$ | 7H |
| 1.76 | (s) | =C—CH$_3$ | |
| 2.00 | (t) | =C—CH$_2$— | 2H |
| 2.16 | (s) | CH$_3$—C(=O)—O— | 3H |
| 5.86 and 7.20 | (m) | Olefinic protons | 2H |

EXAMPLES II–X

The following examples, carried out using the same procedure as Example I, illustrate the results which occur when parameters of the oxidation reaction of beta-ionone with peracetic acid are varied, e.g., as to buffer, solvent, temperature presence of organic base and ratio of organic alkanoic acid to peracetic acid. The percentages given are obtained by gas chromatographic analyses of the reaction mixture after 30 minutes and do not represent yields of isolated material.

| Example No. | % Enol Ester | % Starting Material | % By-Products | Reactants and Reaction Conditions |
|---|---|---|---|---|
| II | 47 | 24 | 29 | Acetic acid- (150 cc) Sodium acetate (20 g) Beta-ionone- (30 g) 40% peracetic acid-(30 g) Temperature: 25° C. |
| III | 12 | 52 | 36 | Acetic acid- (150 g) Beta-ionone- (30 g) 40% peracetic acid-(30 g) Temperature: 25° C. |
| IV | 40 | 29 | 31 | Cyclohexane- (150 cc) Sodium acetate- (20 g) Beta-ionone- (30 g) 40% peracetic acid (30 g) Temperature: 25° C |
| V | 52 | 26 | 22 | Acetic acid- (150 cc) Potassium acetate- (35 g) Beta-ionone- (30 g) 40% peracetic acid (30 g) Temperature: 25° C |
| VI | 31 | 30 | 39 | Formic acid- (150 cc) Potassium acetate- (50 g) |

-continued

| Example No. | % Enol Ester | % Starting Material | % By-Products | Reactants and Reaction Conditions |
|---|---|---|---|---|
| | | | | Beta-ionone- (30 g) 40% peracetic acid (30 g) Temperature: 25° C |
| VII | 49 | 6 | 45 | Acetic acid- (150 cc) Potassium acetate- (35 g) Beta-ionone- (30 g) 40% peracetic acid (33 g) Temperature: 25° C |
| VIII | 36 | 21 | 43 | Acetic acid- (150 cc) Potassium acetate- (35 g) Beta-ionone- (30 g) 40% peracetic acid- (33 g) Temperature: 50° C |
| IX | 0 | 9 | 91 Beta-ionone epoxide | Dimethyl formamide (150 cc) Beta-ionone- (30 g) 40% peracetic acid- (33 g) Temperature: 4 days at a temperature of 18° C |
| X | 55 | 17 | 28 | Acetic acid- (450 cc) Potassium acetate- (105 g) Beta-ionone- (96 g) 40% peracetic acid- (105 g) Temperature: 25° C |

EXAMPLE XI

ROSE FORMULATION

To demonstrate the use of trans beta-cyclohomocitral enol acetate in a rose formulation, the following formula is provided:

| Ingredient | Parts by Weight |
|---|---|
| Phenylethyl alcohol | 200 |
| Geraniol | 400 |
| Trichloromethylphenyl carbinyl acetate | 20 |
| Phenylethyl acetate | 60 |
| Undecylenic aldehyde (10% in diethyl phthalate) | 5 |
| n-Nonyl aldehyde (10% in diethyl phthalate) | 2 |
| Musk ketone | 10 |
| Musk ambrette | 10 |
| Eugenol phenyl acetate | 20 |
| Citronellol | 100 |
| Vanillin (10% in diethyl phthalate) | 6 |
| Eugenol | 30 |
| Citronellyl formate | 30 |
| Geranyl acetate | 10 |
| Linalool | 40 |
| Geranyl phenyl acetate | 50 |
| Cis beta, α-hexenyl acetate | 2 |
| "Trans" beta-cyclohomocitral enol acetate prepared according to Example I | 5 |
| | 1000 |

The addition of 0.5% of beta-cyclohomocitral enol acetate lends a great deal of strength and character to the rose fragrance. It contributes great floralcy and the heady natural sweetness of the red rose flower.

At lower concentrations (0.1%) its contribution is more subtle, however, it still gives an interesting natural effect.

This product may normally be used from approximately 0.01% to 10% in perfume compositions. For special effects, however, higher concentrations (50% plus) can be used.

EXAMPLE XII

PREPARATION OF A SOAP COMPOSITION

100 Grams of soap chips are mixed with one gram of the perfume composition of Example XI until a substantially homogeneous composition is obtained. The perfumed soap composition manifests an excellent rose character with excellent sweet, floral and fruity notes.

EXAMPLE XIII

PREPARATION OF A DETERGENT COMPOSITION

A total of 100 grams of detergent powder is mixed with 0.15 grams of the perfume composition of Example XI, until a substantially homogeneous composition is obtained. This composition has an excellent rose aroma with sweet, floral and fruity notes.

EXAMPLE XIV

RASPBERRY FLAVOR FORMULATION

The following basic raspberry flavor formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |

Trans beta-cyclohomocitral enol acetate is added to half of the above formulation at the rate of 2.0%. The formulation with the beta-cyclohomocitral enol acetate is compared with the formulation without the beta-cyclohomocitral enol acetate at the rate of 0.01 percent (100 ppm) in water and evaluated by a bench panel.

The flavor containing the trans beta-cyclohomocitral enol acetate is found to have substantially sweeter aroma notes and a sweet raspberry, raspberry kernel-like and sweet aftertaste and mouthfeel missing in the basic raspberry formulation. It is the unanimous opinion of the bench panel that the chemical, trans beta-cyclohomocitral enol acetate rounds the flavor out and contributes to a very natural fresh aroma and taste as found in full ripe raspberries. Accordingly, the flavor with the addition of the beta-cyclohomocitral enol acetate is considered as substantially better than the flavor without trans beta-cyclohomocitral enol acetate.

EXAMPLE XV

"Eveready" canned carrot juice, manufactured by the Dole Corporation of San Jose, California, is intimately admixed with 15 ppm of trans beta-cyclohomocitral enol acetate and the resulting mixture is compared with same juice unflavored. The weak aroma and taste of the juice is substantially improved whereby a fresh carrot juice and pleasant sweet note are added thereto. A bench panel of five people prefers the carrot juice flavored with trans beta-cyclohomocitral enol acetate as compared with the unflavored carrot juice.

EXAMPLE XVI

FORMATION OF ALPHA-IONONE EPOXIDE FROM ALPHA-IONONE

Into a 500 ml flask equipped with thermometer, stirrer, addition funnel and reflux condenser, the following materials are placed in the following order:

| Ingredients | Amount |
|---|---|
| Acetic Acid | 150 cc |
| Potassium Acetate | 35 grams |
| Alpha-Ionone | 30 grams |

33 Grams of 40% peracetic acid is then added dropwise into the reaction mass with stirring at 25° C over a 45-minute period. The reaction mass exotherms for approximately 1 hour and is then allowed to remain at room temperature for a period of 15 hours.

The reaction mass is then poured into 500 ml water and the product is extracted with three 150 cc portions of diethyl ether. The ether extracts are combined and washed with two 100 cc portions of saturated sodium chloride solution and dried over anhydrous magnesium sulfate. The residual oil obtained after stripping the solvent, is distilled at 93°–99° C at 0.5 mm Hg pressure yielding 28.3 g of a clean colorless liquid.

IR, MS and NMR analyses confirm the fact that the product is alpha-ionone epoxide having the structure:

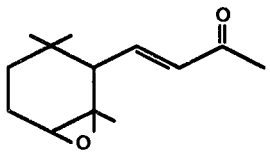

Mass spectral analysis for alpha-ionone epoxide is as follows:

| m/e | Relative Intensity (Order of Most Abundant Ion Indicated in Superscript) |
|---|---|
| 39 | 18 |
| 41 | 30[4] |
| 43 | 100[1] |
| 55 | 20 |
| 95 | 40[3] |
| 109 | 60[2] |
| 111 | 30[5] |
| 151 | 16 |
| 165 | 18 |
| 179 | 23[6] |
| 208 | 9 |

The IR spectrum for alpha-ionone epoxide is set forth in FIG. 32. FIG. 33 is the NMR spectrum for alpha-ionone epoxide.

EXAMPLE XVII

PRODUCTION OF TRANS BETA-CYCLOHOMOCITRAL ENOL ACETATE

Into a 2 liter reaction flask equipped with stirrer, thermometer, addition funnel and cooling bath, the following materials are placed in the following order:

| Ingredients | Amounts |
|---|---|
| Acetic Acid | 450 cc |
| Potassium Acetate | 105 g |
| Beta-Ionone | 96 g |

105 Grams of 40% peracetic acid is then added dropwise to the reaction mass with cooling while maintaining the reaction mass at 25° C ± 2° C over a period of two hours. The reaction mass is then stirred for an additional 3-hour period (during the first hour a slight exotherm occurs) at 25° C.

The reaction mass is then poured into 1,000 ml water and the resultant product is extracted with three 300 cc volumes of diethyl ether. The ether extracts are combined and washed with two 150 cc portions of saturated sodium chloride solution. The resultant washed ether extract is then evaporated whereby 118 grams of residual oil is obtained. NMR, IR and Mass Spectral analyses confirm that the resulting material is trans beta-cyclohomocitral enol acetate.

EXAMPLE XVIII

TOBACCO FORMULATION

A tobacco mixture is produced by admixing the following ingredients:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 or 1,000 ppm of trans beta-cyclohomocitral enol acetate produced according to the process of Example XVII. The control cigarettes not containing the trans beta-cyclohomocitral enol acetate and the experimental cigarettes which contain the trans beta-cyclohomocitral enol acetate produced according to the process of Example XVII are evaluated by paired comparison and the results are as follows:

The experimental cigarettes are found, on smoking, to have more "body" and to be sweeter, more aromatic, more tobacco-like and less harsh with sweet, floral and fruity notes.

The tobacco of the experimental cigarettes, prior to smoking, has sweet, floral and fruity notes. All cigarettes are evaluated for smoke flavor with a 20 mm cellulose acetate filter.

The trans beta-cyclohomocitral enol acetate produced according to the process of Example XVII enhances the tobacco like taste and aroma of the blended cigarette imparting to it sweet, natural tobacco notes.

EXAMPLE XIX

PREPARATION OF A COSMETIC-POWDER COMPOSITION

A cosmetic powder is prepared by mixing in a ball mill, 100 g of talcum powder with 0.25 g of trans beta-cyclohomocitral enol acetate prepared according to Example XVII. It has an excellent sweet, floral, fruity aroma.

EXAMPLE XX

PERFUMED LIQUID DETERGENT

Concentrated liquid detergents with a sweet, floral, fruity odor are prepared containing 0.10%, 0.15% and 0.20% of trans beta-cyclohomocitral enol acetate prepared according to Example XVII. They are prepared by adding and homogeneously mixing the appropriate quantity of trans beta-cyclohomocitral enol acetate in the liquid detergent. The detergents all possess a sweet, floral, fruity fragrance, the intensity increasing with greater concentrations of trans beta-cyclohomocitral enol acetate.

EXAMPLE XXI

PREPARATION OF A COLOGNE AND HANDKERCHIEF PERFUME

Trans beta-cyclohomocitral enol acetate prepared according to the process of Example XVII is incorporated in a cologne at a concentration of 2.5% in 85% aqueous ethanol; and into a handkerchief perfume at a concentration of 20% (in 95% aqueous ethanol). A distinct and definite sweet, floral, fruity fragrance is imparted to the cologne and to the handkerchief perfume.

EXAMPLE XXII

PREPARATION OF A COLOGNE AND HANDKERCHIEF PERFUME

The composition of Example XI is incorporated in a cologne at a concentration of 2.5% in 85% aqueous ethanol; and into a handkerchief perfume at a concentration of 20% (in 95% aqueous ethanol). The use of the beta-cyclohomocitral enol acetate in the composition of Example XI affords a distinct and definite strong rose aroma with sweet, floral, fruity notes to the handkerchief perfume and cologne.

EXAMPLE XXIII

PREPARATION OF SOAP COMPOSITION

One hundred grams of soap chips are mixed with one gram of trans beta-cyclohomocitral enol acetate until a substantially homogeneous composition is obtained. The perfumed soap composition manifests an excellent sweet, floral, fruity aroma.

EXAMPLE XXIV

PREPARATION OF A DETERGENT COMPOSITION

A total of 100 g of a detergent powder is mixed with 0.15 g of the trans beta-cyclohomocitral enol acetate of Example XVII until a substantially homogeneous composition is obtained. This composition has an excellent sweet, floral, fruity aroma.

EXAMPLE XXV

Perpropionic acid is prepared in the following manner. A mixture of the following materials:

| 160 ml propionic acid | Referred to hereinafter as "Mixture A" |
| 1 ml sulfuric acid (concentrated) | |
| 40 g 50% hydrogen peroxide | | is allowed to stand for 20 hours at room temperature.

The following reactants are placed in a 500 ml reaction flask equipped with a stirrer and cooling bath:

| 140 ml propionic acid | Referred to hereinafter as "Mixture B" |
| 75 g potassium acetate | |
| 60 g beta-ionone | |

To the stirred Mixture B is added, dropwise, Mixture A over a 60-minute period while maintaining the reaction temperature at 25° ± 2° C by means of external cooling. When the addition is complete the reaction mixture is stirred for an additional 2 hours at 25° C.

The reaction mixture is then poured into 1,000 ml water and extracted twice with 250 ml portions of diethyl ether. The combined ether extracts are then washed first with water (three 100 ml portions) and then with a saturated solution of sodium chloride (150 ml). The ether solution is then dried over anhydrous magnesium sulfate and the solvent evaporated to yield 78 g of crude oil containing propionic acid as well as the product, trans beta-cyclohomocitral enol acetate.

The GLC profile for the resulting material is set forth in FIG. 34 (GLC conditions: 10 feet × ¼ inch 10% Carbowax 20M column, operated at 220° C isothermal).

EXAMPLE XXVI

Performic acid is prepared in the following manner: 20 g 50% hydrogen peroxide and 80 ml of formic acid is admixed and the reaction mass is left at room temperature for 1.5 hours.

To a mixture consisting of 50 g of potassium acetate, 70 ml of acetic acid and 30 g of beta-ionone is added the preformed performic acid, prepared as described above, dropwise over a 30 minute period while maintaining the temperature of the stirred reaction mass at 25° C by means of external cooling. After the addition is complete, the mixture is stirred for a further 90 minutes at 25° C and is then poured into 800 ml of water. The product is extracted with two 200 ml portions of diethyl ether. The ether extracts are combined, washed with two 150 ml portions of saturated sodium chloride solution and then dried. Removal of the solvent by evaporation yields 32.5 g crude oil.

A gas chromatographic analysis of this material shows the following compositions:

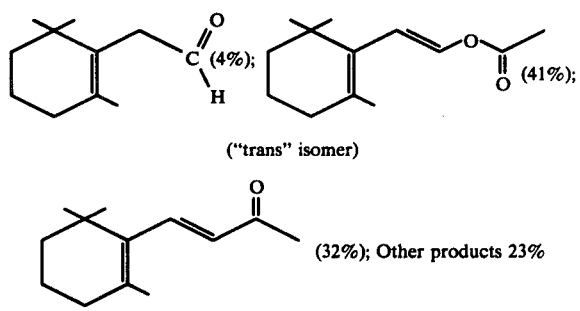

("trans" isomer)

(4%); (41%); (32%); Other products 23%

EXAMPLE XXVII

A. POWDER FLAVOR COMPOSITION

20 Grams of the flavor composition of Example XIV is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F., and a wheel speed of 50,000 r.p.m.

B. SUSTAINED RELEASE FLAVOR

The following mixture is prepared:

| Ingredient | Parts by Weight |
|---|---|
| Liquid Raspberry Flavor Composition of Example XIV | 20 |
| Propylene glycol | 9 |
| Cab-O-Sil ®M-5 (Brand of Silica produced by the Cabot Corporation of 125 High Street, Boston, Mass. 02110; Physical Properties: Surface Area: 200 m²/gm Nominal Particle size: 0.012 microns Density: 2.3 lbs/cu.ft.) | 5.00 |

The Cab-O-Sil is dispersed in the liquid raspberry flavor compositions of Example XIV with vigorous stirring, thereby resulting in a viscous liquid. 71 Parts by weight of the powder flavor composition of Part A, supra, is then blended into the said viscous liquid, with stirring at 25° C for a period of 30 minutes resulting in a dry, free flowing sustained release flavor powder.

EXAMPLE XXVIII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XIV is added to the solution which is then homogenized to form an emulsion having particle size typically in the range of 2-5 L microns. This material is kept at 120° F. under which conditions the gelatin will not jell.

Coascervation is induced by adding, slowly and uniformly 40 parts by weight of a 20% aqueous solution of sodium sulphate. During coascervation, the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XXIX

CHEWING GUM 100 parts by weight of chicle are mixed with 4 parts by weight of the flavor prepared in accordance with Example XXVII. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry flavor.

EXAMPLE XXX

CHEWING GUM 100 parts by weight of chicle are mixed with 18 parts by weight of the flavor prepared in accordance with Example XXVIII. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry flavor.

EXAMPLE XXXI

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XXVII |
| 100.00 (Total) | |

PROCEDURE:

-continued

| Parts by Weight | Ingredient |
|---|---|

1. The ingredients in Group "A" are stirred and heated in a steam jacketed kettle to 160° F.
2. Stirring is continued for an additional three to five minutes to form a homogenous gel.
3. The powders of Group "B" are added to the gel, while mixing until a homogenous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant raspberry flavor, of constant strong intensity throughout said procedure (1-1.5 minutes).

EXAMPLE XXXII

CHEWABLE VITAMIN TABLETS

The flavor material produced according to the process of Example XIX is added to a Chewable Vitamin Tablet Formulation at a rate of 10 gm/Kg which Chewable Vitamin Tablet Formulation is prepared as follows:

In a Hobart Mixer, the following materials are blended to homogeneity:

| | Gms/1000 tablets |
|---|---|
| Vitamin C (ascorbic acid) as ascorbic acid-sodium ascorbate mixture 1:1 | 70.0 |
| Vitamin B₁ (thiamine mononitrate) as Rocoat ®thiamine mononitrate 33⅓ % (Hoffman La Roche) | 4.0 |
| Vitamin B₂ (riboflavin) as Rocoat ®riboflavin 33⅓ % | 5.0 |
| Vitamin B₆ (pyridoxine hydrochloride) as Rocoat ®pyridoxine hydrochloride 33⅓ % | 4.0 |
| Niacinamide as Rocoat ®niacinamide 33⅓ % | 33.0 |
| Calcium pantothenate | 11.5 |
| Vitamin B₁₂ (cyanocobalamin) as Merck 0.1 % in gelatin | 3.5 |
| Vitamin E (dl-alpha tocopheryl acetate) as dry Vitamin E acetate 33⅓ % Roche | 6.6 |
| d-Biotin | 0.044 |
| Certified lake color | 5.0 |
| Flavor of Example XXVIII | (as indicated above) |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong raspberry flavor for a period of 12 minutes.

EXAMPLE XXXIII

CHEWING TOBACCO

Onto 100 pounds of tobacco for chewing (85% Wisconsin leaf and 15% Pennsylvania leaf) the following casing is sprayed at a rate of 30%:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example XXVII | 0.4 |

The resultant product is redried to a moisture content of 20%. On chewing, this tobacco has an excellent substantially consistent, long-lasting raspberry (20 minutes) nuance in conjunction with the main fruity tobacco note.

EXAMPLE XXXIV

PRODUCTION OF BETA-CYCLOHOMOCITRAL ENOL BUTYRATE

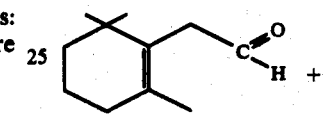

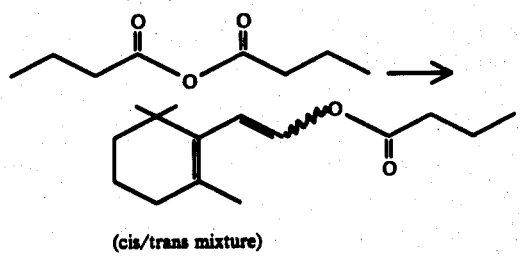

(cis/trans mixture)

Into a 100 ml reaction flask are added the following materials:

| Ingredients | Quantity |
|---|---|
| beta-cyclohomocitral | 16.6 g (0.1 moles) |
| butyric anhydride | 27 g (0.17 moles) |
| potassium acetate | 1 g (0.01 moles) |

The reaction mass is heated at a temperature of 170° C for a period of 9.5 hours. At this period in time GLC analysis indicates the substantially total disappearance of the beta-cyclohomocitral and the formation of two new peaks. GC-MS analysis indicates that the peaks represent the cis and trans isomers of beta-cyclohomocitral enol butyrate having, respectively, the structures:

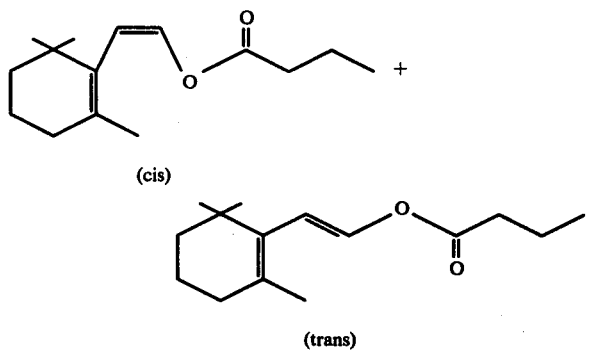

(cis)

(trans)

Figure 1:
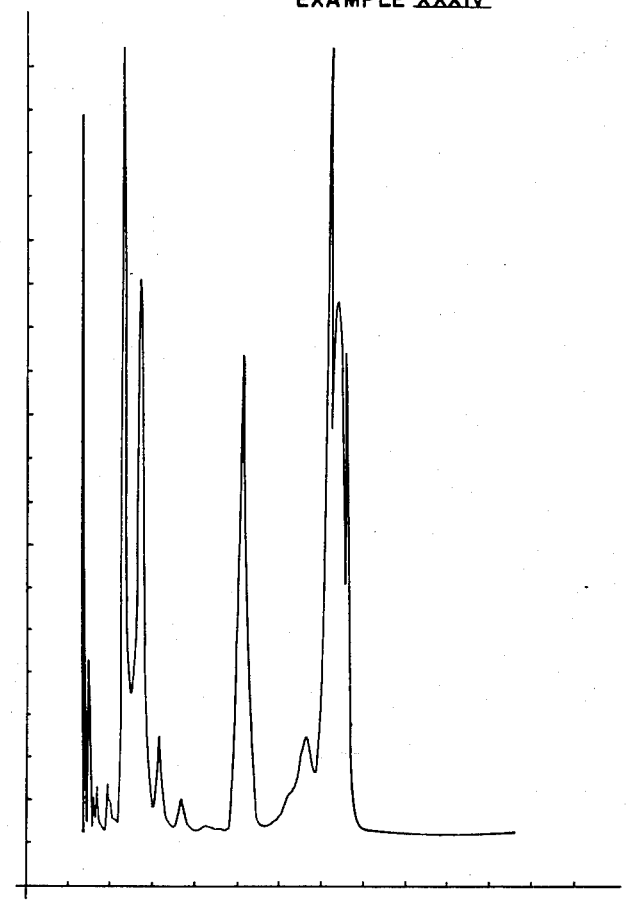
FIG. 1 is the GLC profile for the reaction product of Example XXXIV wherein cis and trans beta-cyclohomocitral enol butyrate is produced.

The GLC profile is set forth in FIG. 1 (conditions: 10 feet × ⅛ inch Carbowax 20M column, programmed from 80°–180° C at 4° C per minute).

Figure 2:
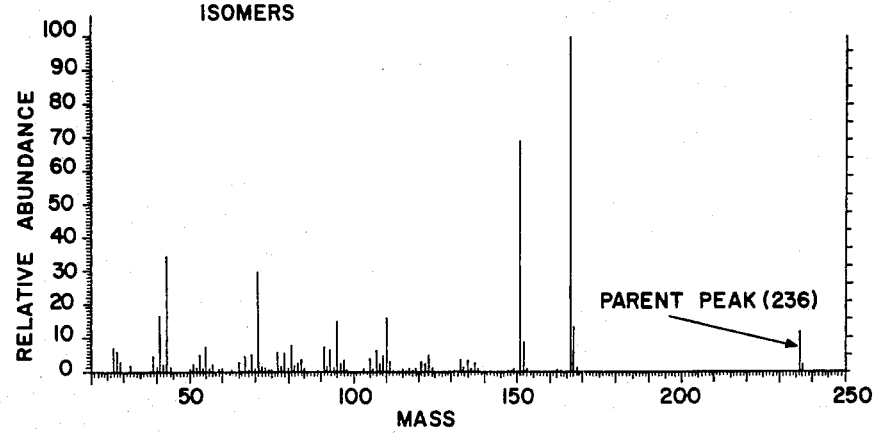
FIG. 2 is the GC-MS profile for the reaction product produced in Example XXXIV.

The GC-MS profile is set forth in FIG. 2.

The NMR analysis of the cis isomer of beta-cyclohomocitral enol butyrate is as follows:

| 0.97 ppm | singlet superimposed on triplet | $\begin{matrix} CH_3 \\ \phantom{xx}\diagdown | \\ \phantom{xxx}C- \\ \phantom{xx}\diagup \\ CH_3 \end{matrix}$ and $CH_3-\underset{\underset{O}{\|}}{C}-\overset{O}{\overset{\|}{C}}-$ | 9H |
|---|---|---|---|
| 1.54 | broad singlet | $=C-CH_3$ | |
| 1.78–1.21 | multiplet | $-(CH_2)_{\overline{3}}$ | } 9H |
| 2.00 | diffuse triplet | $=C-CH_2-$ | 2H |
| 2.35 | triplet | $-CH_2-\overset{O}{\overset{\|}{C}}-O-$ | 2H |
| 5.32 | doublet (J=7Hz,cis) | $HC=\underset{\|}{\overset{H}{C}}-O-$ | 1H |
| 7.06 | doublet | | 1H |

The NMR spectrum for the cis isomer of beta-cyclohomocitral enol butyrate is set forth in FIG. 3.

The Infrared analysis for the cis isomer of beta-cyclohomocitral enol butyrate is as follows:

740, 1085, 1160, 1230, 1360, 1750, 2870, 2940, 2960 cm$^{-1}$

The Infrared spectrum for the cis isomer of beta-cyclohomocitral enol butyrate is set forth in FIG. 4.

The Infrared analysis for the trans isomer of beta-cyclohomocitral enol butyrate is as follows:

930, 1100, 1160, 1230, 1360, 1750, 2870, 2940, 2960 cm$^{-1}$

Figure 5:
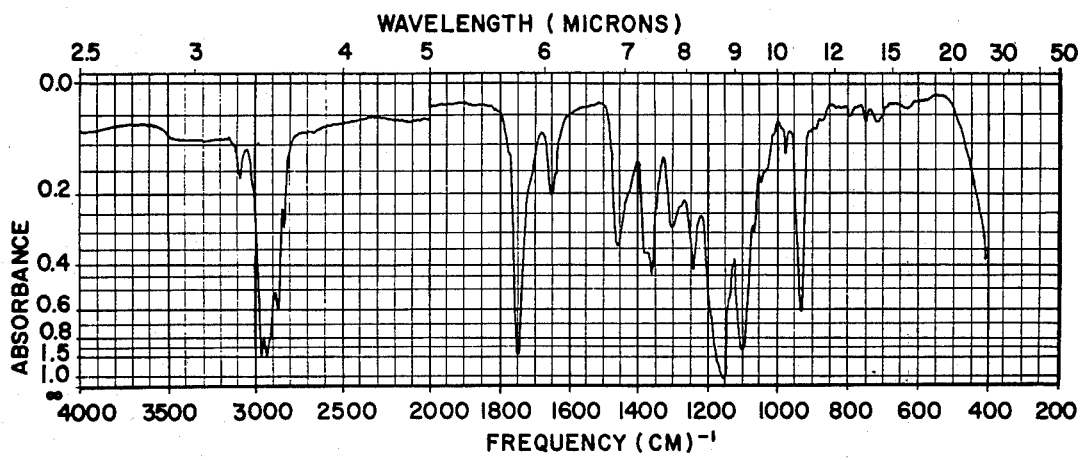
FIG. 5 is the IR spectrum for the trans isomer of beta-cyclohomocitral enol butyrate produced according to Example XXXIV.

The Infrared analysis for the trans isomer of beta-cyclohomocitral enol butyrate is set forth in FIG. 5.

The NRM spectrum for the trans isomer of beta-cyclohomocitral enol butyrate is set forth as follows:

| 1.00 ppm | doublet superimposed on triplet | $\left\{\begin{matrix} CH_3 \\ \phantom{xx}\diagdown | \\ \phantom{xxx}C- \\ \phantom{xx}\diagup \\ CH_3 \phantom{xx} + \\ CH_3-CH_2- \end{matrix}\right\}$ | 9H |
|---|---|---|---|
| 1.82–1.43 | multiplet | $\begin{matrix}=C-CH_3- \\ + \\ -(CH_2)_{\overline{4}}\end{matrix}$ | 11H |
| 2.00 | diffuse triplet | $=C-CH_2-$ | 2H |
| 2.40 | triplet | $-CH_2-\underset{\underset{O}{\|}}{\overset{O}{\overset{\|}{C}}}-O-$ | 2H |
| 5.86 | doublets (J = 13 Hz, trans) | $HC=\underset{\|}{\overset{H}{C}}-O-\overset{O}{\overset{\|}{C}}-$ | 2H |
| 7.02 | | | |

Figure 6:
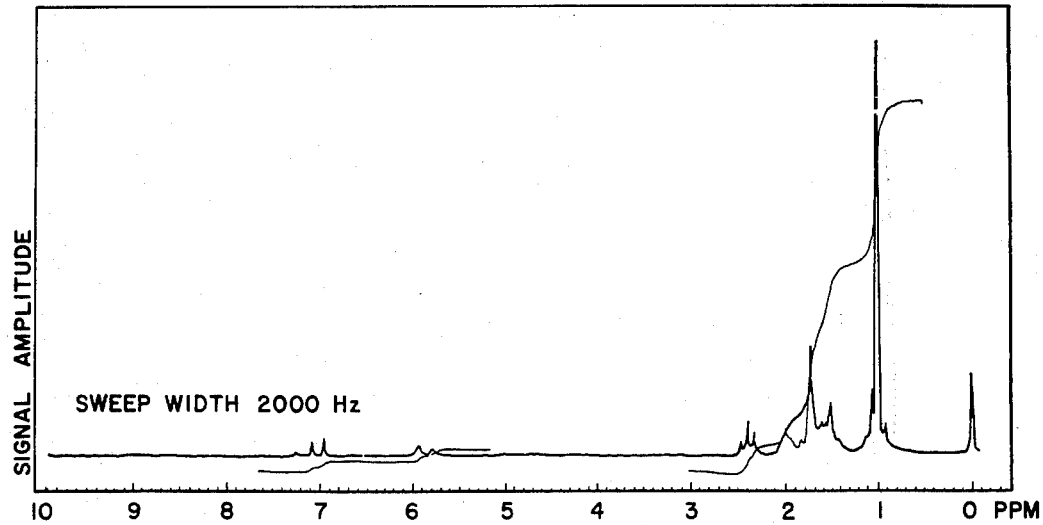
FIG. 6 is the NMR spectrum for the trans isomer of beta-cyclohomocitral enol butyrate produced according to Example XXXIV.

The NRM spectrum for the trans isomer of beta-cyclohomocitral enol butyrate is set forth in FIG. 6.

The crude reaction mass produced as described supra is admixed with 100 ml diethyl ether. The resulting diethyl ether solution is washed with two 100 ml portions of water and one 25 ml portion of saturated sodium bicarbonate. The washed ether solution is dried over anhydrous magnesium sulfate, filtered and stripped on a Rotovap evaporator yielding 32.4 g of product containing a significant amount of enol butyrate. The components are separated by preparative GLC.

The trans beta-cyclohomocitral enol butyrate at 2 ppm has a sweet, rosey, fruity aroma. At 5 ppm it has a sweet/rosey, rosebud, rosey/fruity aroma and a rosey/-fruity taste. At 20 ppm it has a sweet/rosey/fruity aroma and taste with a delicate damascenone-like character.

The cis beta-cyclohomocitral enol butyrate at 0.2 ppm only has a bitter aftertaste. At 2 ppm it has a weak rosey aroma. At 6 ppm it has a weak, rosey aroma and bitter aftertaste.

EXAMPLE XXXV

PRODUCTION OF BETA-CYCLOHOMOCITRAL ENOL BUTYRATE

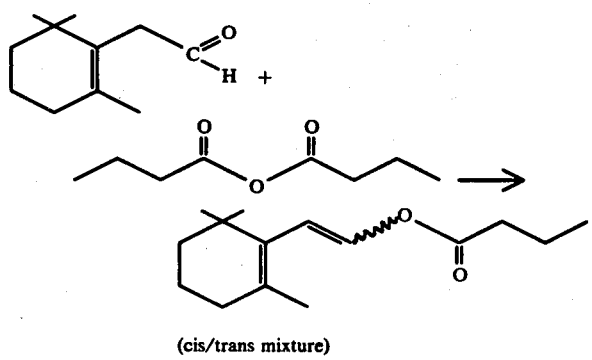

(cis/trans mixture)

Into a 100 ml reaction flask are charged the following materials:

| Ingredients | Quantity |
|---|---|
| beta-cyclohomocitral | 16.6 g (0.1 mole) |
| paratoluene sulfonic acid | 0.5 g (0.03 moles) |
| butyric anhydride | 39.5 g (0.25 mole) |

The reaction mass is heated with stirring to 170° C and maintained at 170° C for a period of 9.5 hours. At the end of this time GLC analysis indicates a substantial proportion of beta-cyclohomocitral enol butyrate (conditions: 4 feet × ⅛ inch Carbowax 20 M column, programmed from 80°-180° C at 4° C per minute).

Figure 7:
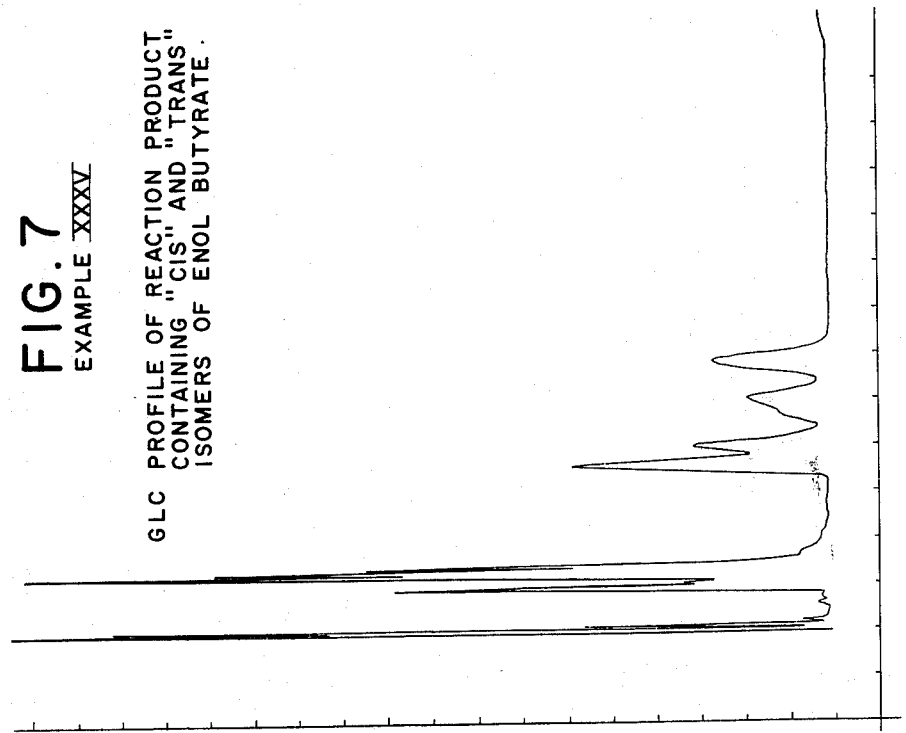
FIG. 7 is the GLC profile for the reaction product containing beta-cyclohomocitral enol butyrate produced according to Example XXXV.
Figure 10:
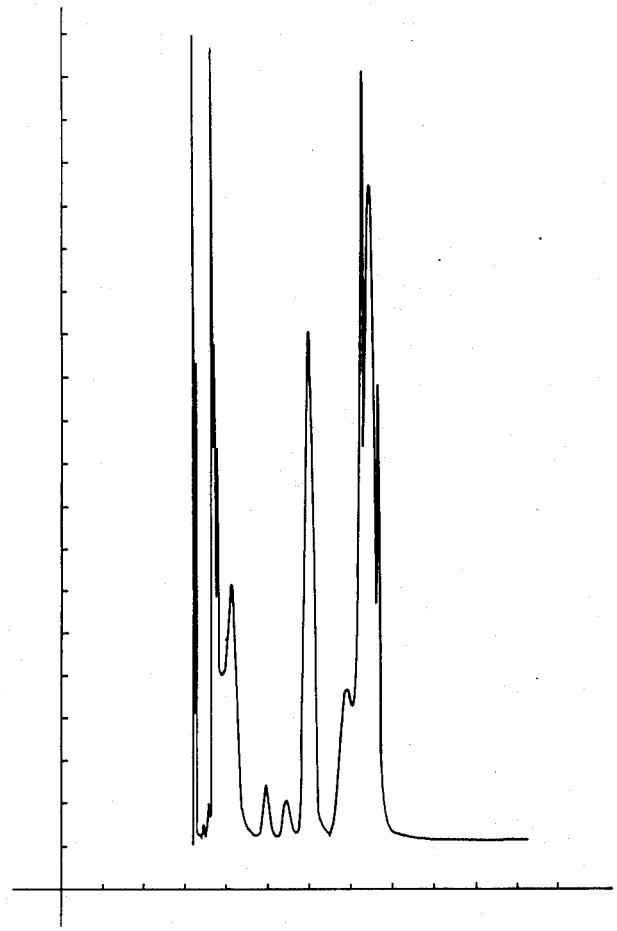
FIG. 10 is the GLC profile for the beta-cyclohomocitral enol isobutyrate produced according to Example XXXVII.

The GLC profile is set forth in FIG. 7.

The GLC profile indicates a substantial amount of cis isomer and a substantial amount of trans isomer. NRM and mass spectral analyses confirm that peak "D" of FIG. 7 is the cis isomer and peak "E" is the trans isomer.

The crude material is admixed with 100 ml of ether and the resulting ether solution is washed with two 100 ml portions of water followed by one 25 ml portion of sodium bicarbonate. The washed ether solution is then dried over anhydrous magnesium sulfate, filtered and stripped using a "Rotovap" evaporator. The resulting product is 32.4 g product containing a significant proportion of beta-cyclohomocitral enol butyrate. The products are separated by preparative GLC.

EXAMPLE XXXVI

PRODUCTION OF BETA-CYCLOHOMOCITRAL ENOL BUTYRATE

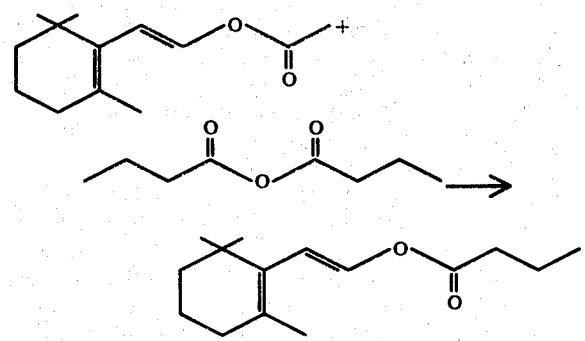

Into a 25 ml reaction flask the following materials are added:

| Ingredients | Quantity |
|---|---|
| beta-cyclohomocitral enol acetate produced according to Example I | 2.0 g (0.008 moles) |
| butyric anhydride | 2.5 g (0.016 moles) |
| paratoluene sulfonic acid | trace |

The reaction mass is heated with stirring at a temperature of 170° C and maintained at that temperature for a period of 8 hours. At the end of this 8 hour period, GLC analysis indicates the presence of a substantial quantity of trans beta-cyclohomocitral enol butyrate. This is confirmed by NMR and mass spectral analyses.

Figure 8:
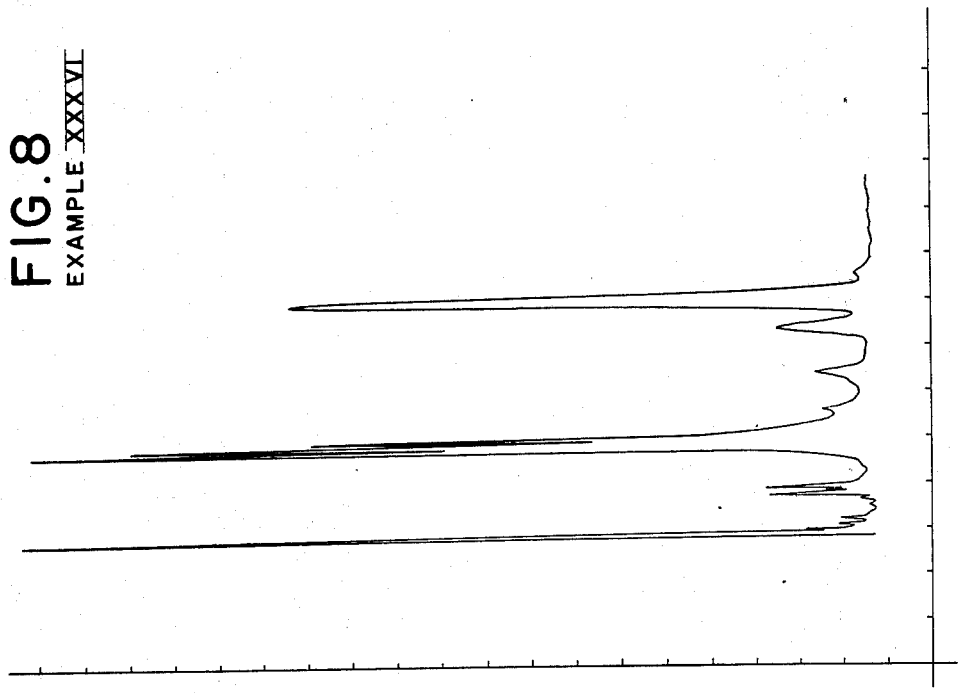
FIG. 8 is the GLC profile for the beta-cyclohomocitral enol butyrate produced according to Example XXXVI.

The GLC profile for the reaction product at the point in time is set forth in FIG. 8.

Figure 9:
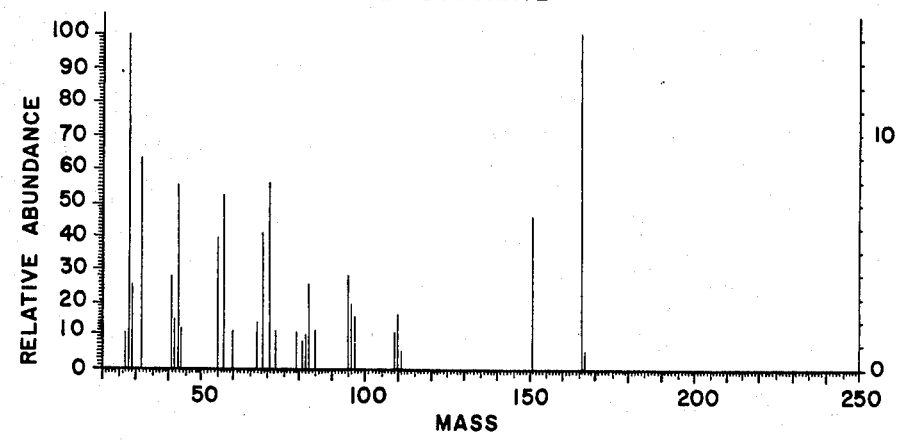
FIG. 9 is the GC-MS profile for beta-cyclohomocitral enol butyrate produced according to Example XXXVI.

The GC-MS profile is set forth in FIG. 9.

25 ml diethyl ether is admixed with crude product and the ether solution is washed with two 25 ml portions of water and one 25 ml portion of sodium bicarbonate. The washed ether solution is then dried over anhydrous magnesium sulfate, filtered and stripped on a Rotovap evaporator thus yielding a product containing a significant proportion of trans beta-cyclohomocitral enol butyrate.

EXAMPLE XXXVII

PRODUCTION OF BETA-CYCLOHOMOCITRAL ENOL ISOBUTYRATE

Reaction:

Reaction:

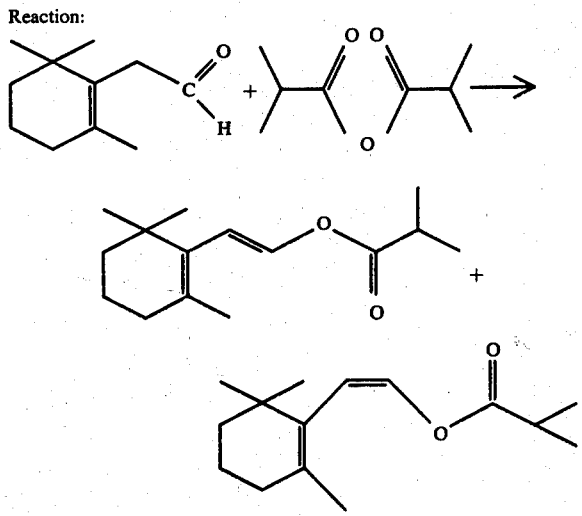

Into a 100 ml reaction flask equipped with stirrer, thermometer and reflux condenser are placed the following ingredients:

| Ingredients | Quantity |
|---|---|
| beta-cyclohomocitral | 16.6 g (0.1 mole) |
| isobutyric anhydride | 27 g (0.17 mole) |
| potassium acetate | 12 g (0.01 mole) |

The reaction mass is heated at a temperature of 169° C for a period of 13 hours. The reaction mixture turns dark and 100 ml of diethyl ether is added to the mixture. The reaction mass is then washed with two 100 ml portions of water and one 100 ml portion of saturated aqueous sodium bicarbonate. The organic layer is then dried over anhydrous magnesium sulfate, filtered and stripped of solvent on a Rotovap yielding 35.5 g of crude product. The GLC profile of the crude product indicates that only a trace quantity of beta-cyclohomocitral remains with two product peaks having a longer retention time being formed. The GLC profile for the reaction product at this point in time is set forth in FIG. 19 (conditions: 10 feet × ⅛ inch Carbowax 20M column, programmed from 80°-180° C at 4° C per minute).

Figure 11:
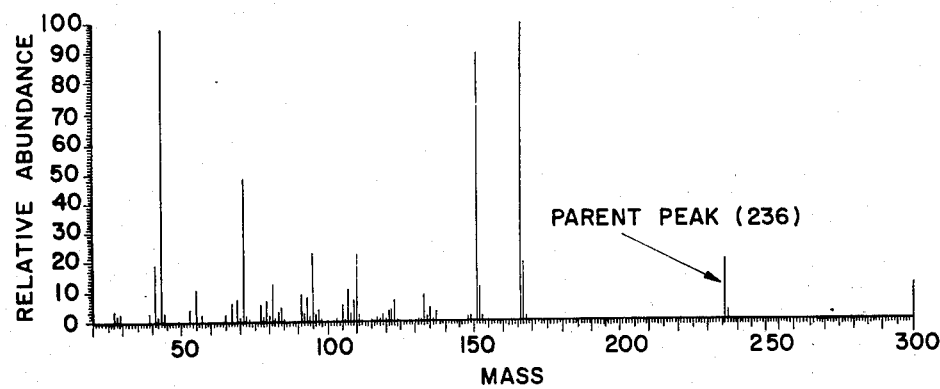
FIG. 11 is the GC-MS profile for the best-cyclohomocitral enol isobutyrate produced according to Example XXXVII.

The GC-MS profile is set forth in FIG. 11.

Figure 12:
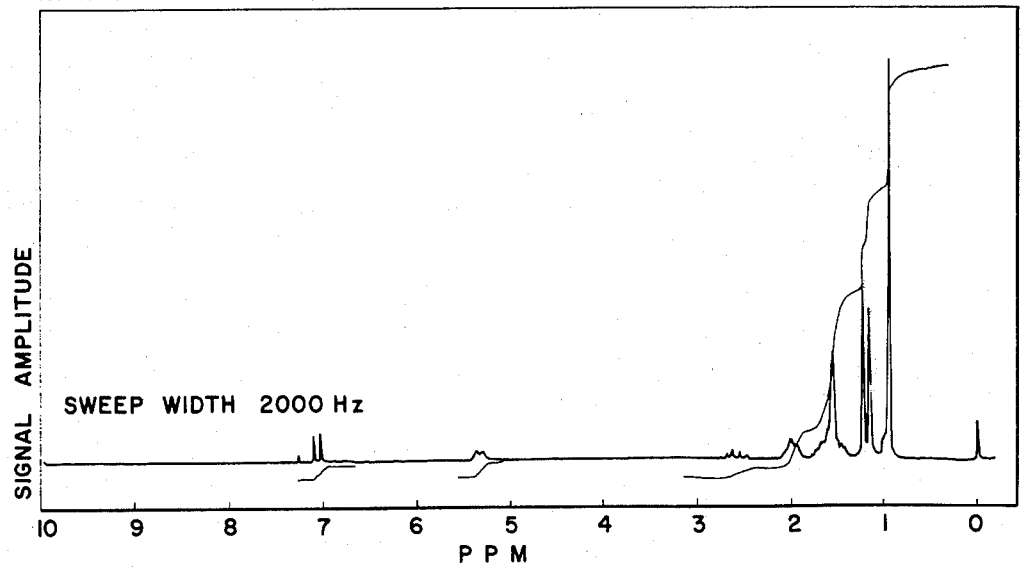
FIG. 12 is the NMR spectrum for the cis isomer of betacyclohomocitral enol isobutyrate produced according to Example XXXVII.
Figure 13:
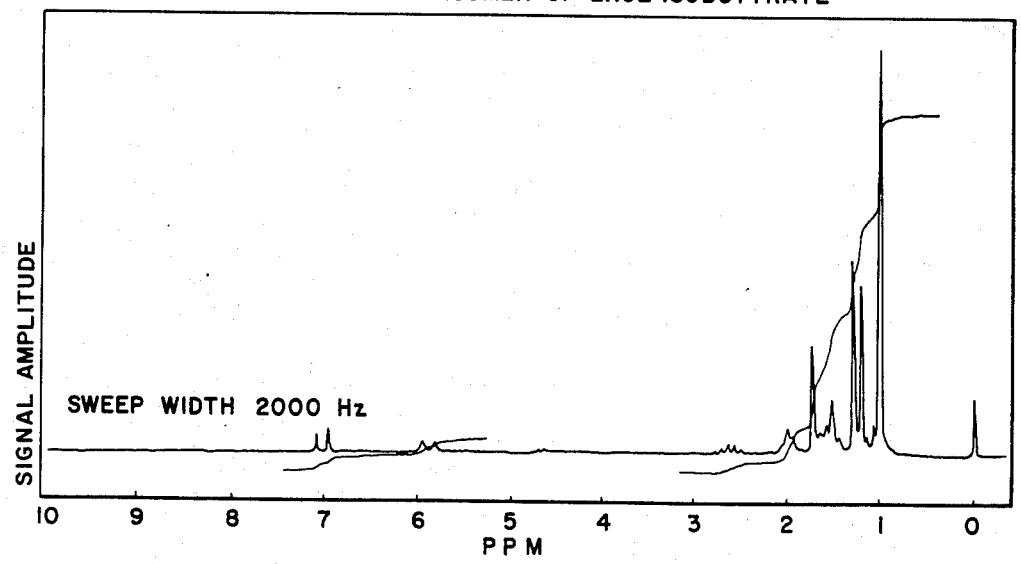
FIG. 13 is the NMR spectrum for the trans isomer of beta-cyclohomocitral enol isobutyrate produced according to Example XXXVII.

The materials composing the two major peaks are isolated by preparative GLC and are analyzed using NMR analysis, peak 1 being confirmed to be the ci isomer of beta-cyclohomocitral enol isobutyrate and peak 2 being confirmed to be the trans isomer of beta-cyclohomocitral enol isobutyrate. The NMR spectrum for the cis isomer is set forth in FIG. 12. The NMR spectrum for the trans isomer is set forth in FIG. 13.

The trans isomer of beta-cyclohomocitral enol isobutyrate, insofar as its flavor properties are concerned, has a sweet, woody, rosey, fruity, "wood-rosin", spicey, apple juice aroma with fruity, apple/raspberry, woody, sweet, wood-rosin, tea and astringent flavor characteristics. Insofar a its perfumery uses are concerned, it has an acidic, fruity, damascenone-like aroma with strong animal tobacco nuances; stronger than those of the "cis" isomer.

The cis isomer of beta-cyclohomocitral enol isobutyrate, insofar as its flavor properties are concerned, has a sweet, oriental/olibanum, "delicate rosey", fruity, ionone-like, clove, camphoraceous aroma with rosey, woody, clove, mimosa, ionone, musty and camphoraceous flavor characteristics. The perfume properties of the cis isomer are such that it has a sweet, woody, green tobacco aroma with fruity and resinous notes; but is is not quite a fruity as the trans isomer. The cis isomer also has strong ionone, mimosa nuances.

It is noteworth that the cis and trans isomers have uses in food flavors different from one another. The cis isomer is useful in clve and cinnamon flavors whereas the trans isomer is useful in apple juice, tea, raspberry and honey flavors.

EXAMPLE XXXVIII

PRODUCTION OF BETA-CYCLOHOMOCITRAL ENOL OCTANOATE

Reaction:

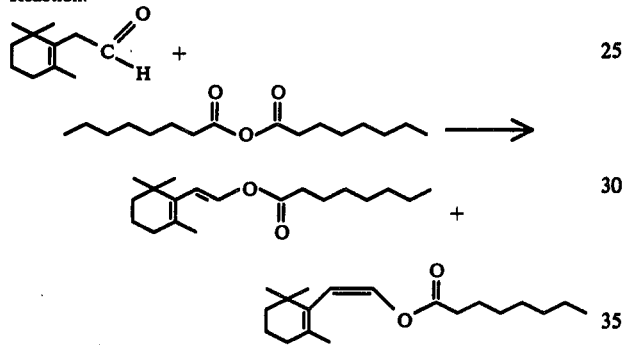

Into a 100 ml reaction flask equipped with stirrer, thermometer and reflux condenser is placed the following ingredients:

| Ingredients | Quantity |
| --- | --- |
| beta-cyclohomocitral | 16.6 g (0.1 mole) |
| octanoic anhydride | 41 g (0.17 mole) |
| potassium acetate | 1 g (0.01 mole) |

Figure 14:
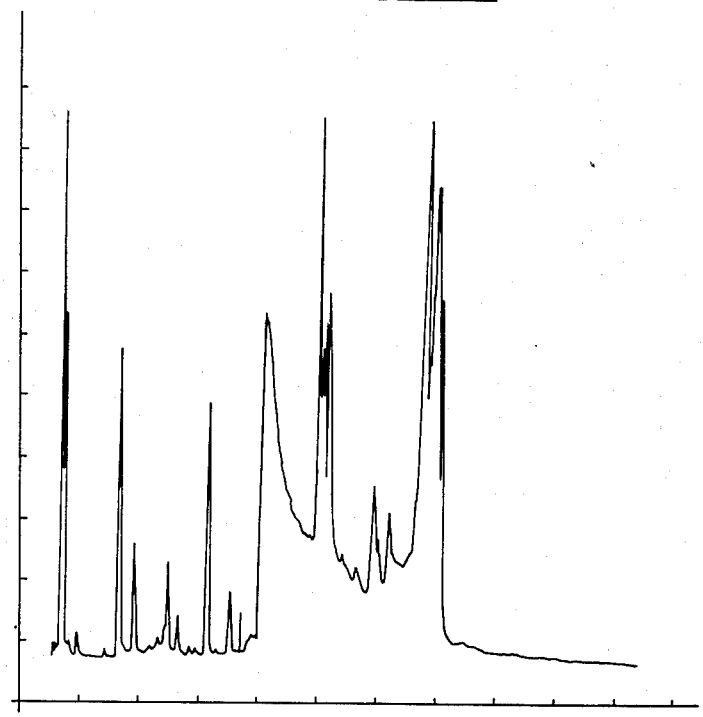
FIG. 14 is the GLC profile for the beta-cyclohomocitral enol octanoate produced according to Example XXXVIII.

The reaction mass is heated for a period of 11 hours at a temperature in the range of from 170°–190° C. At the end of the 11 hour period 100 ml of diethyl ether is added to the reaction mass after cooling the reaction mass to room temperature. The resulting mixture is then washed with two 100 ml portions of water and one 100 ml portion of saturated aqueous sodium bicarbonate. The organic layer is separated from the aqueous layer; then dried over anhydrous magnesium sulfate, filtered and stripped of solvent on a Rotovap yielding 31.4 g of oil. GLC analysis of the crude material indicates several peaks. The GLC profile is set forth in FIG. 14. The GLC conditions are the same as those which are set forth in Example XXXVII.

Figure 15:
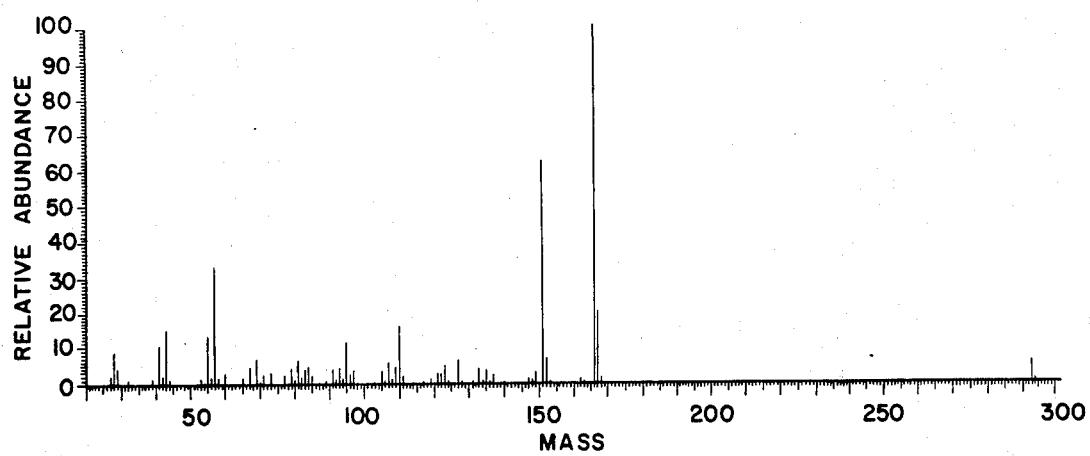
FIG. 15 is the GC-MS profile for the beta-cyclohomocitral enol octanoate produced according to Example XXXVIII.

The GC-MS profile for the reaction product is set forth in FIG. 15.

Two major peaks are trapped and NMR analysis confirms that one of the peaks is cis-beta-cyclohomocitral enol octanoate and the other peak is trans-beta-cyclohomocitral enol octanoate.

Figure 16:
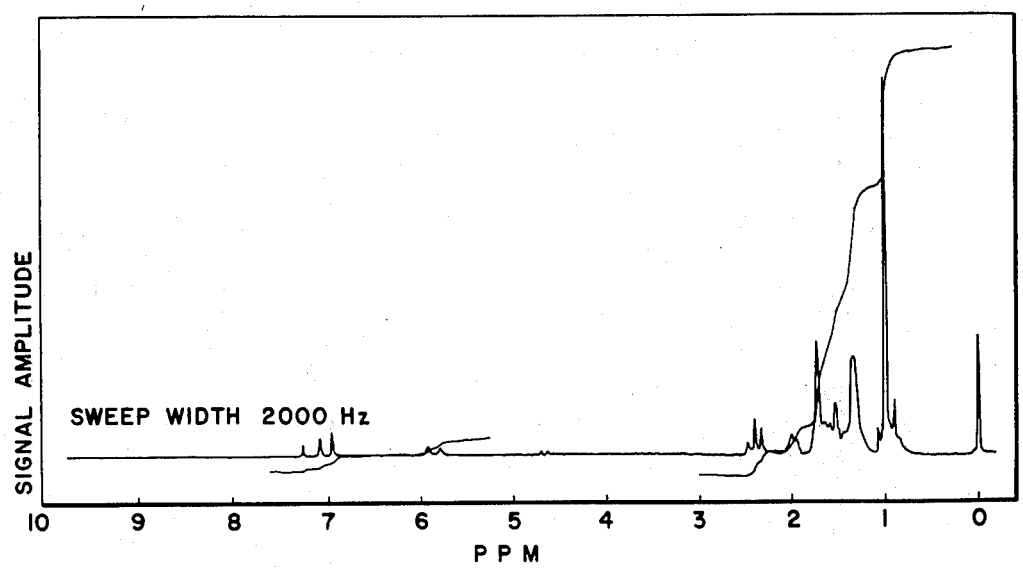
FIG. 16 is the NMR spectrum for the trans isomer of beta-cyclohomocitral produced according to Example XXXVIII.
Figure 17:
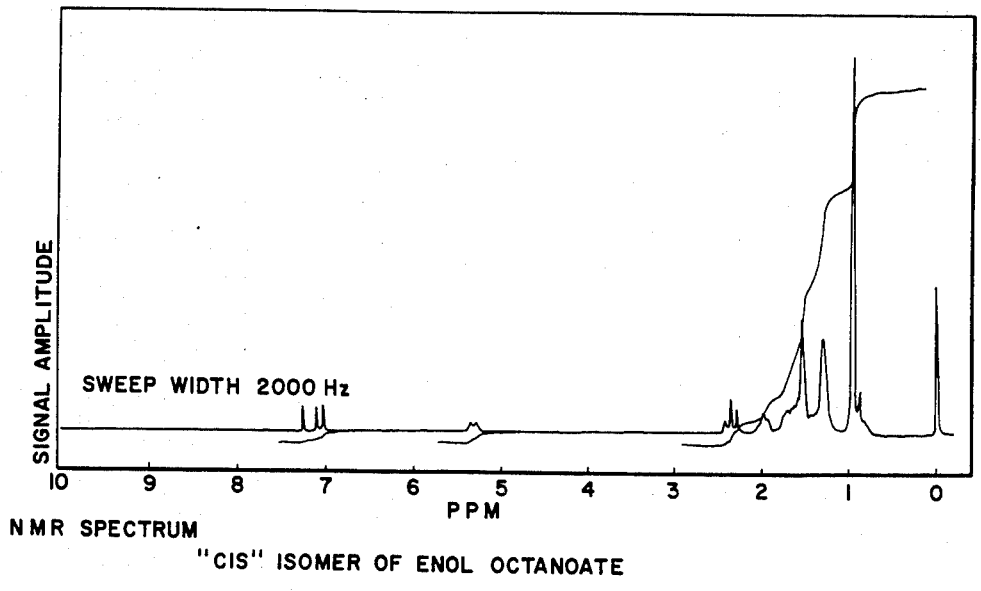
FIG. 17 is the NMR spectrum for the cis isomer of beta-cyclohomocitral produced according to Example XXXVIII.

FIG. 16 is the NMR spectrum for the trans isomer of beta-cyclohomocitral enol octanoate. FIG. 17 is the NMR spectrum for the cis isomer of beta-cyclohomocitral enol octanoate.

The cis isomer, from a flavor evaluation standpoint, has a sweet, rosey, damascenone-like, dried fruit, cocoa aroma and a sweet, delicate rosey, damascenone-like, tea, apple-juice-like, tobacco flavor character. The trans isomer has an ionone-like, woody aroma character with an ionone-like, woody, musty and astringent flavor character. The cis isomer is much preferred over the trans isomer for flavor use.

From a perfumey standpoint the cis isomer has a woody, cheesy, fatty, rather acrid aroma with some ionone nuances. The trans isomer has a woody, cheesy, fatty aroma with more of a warm, fruity note than does the cis iosmer with cognac, balsamic and tobacco nuances, however, the cheesy note dominates.

EXAMPLE XXXIX

ROSE FORMULATION

The following mixture is prepared:

| Ingredient | Parts by Weight |
| --- | --- |
| Citronellal | 60 |
| Geraniol | 40 |
| Citronellyl formate | 5 |
| Geranyl acetate | 3 |
| Phenylethyl alcohol | 20 |
| Phenyl acetic acid | 3 |
| Methyl phenyl acetate | 1 |
| Phenylethyl acetate | 2 |
| 4-(4-methyl-4-hydroxy)Δ³-cyclohexene carboxaldehyde | 3 |
| Linalool | 6 |
| Eugenol | 2 |
| Mixture of "cis" and "trans" beta-cyclohomocitral enol isobutyrate produced according to the process of Example XXXVII | 5 |

The mixture of cis and trans beta-cyclohomocitral enol isobutyrate produced according to Example XXXVII imparts to this rose formulation a sweet, fruity, damascenone-like quality thus imparting thereto an unexpected, unobvious and advantageous "lift".

EXAMPLE XL

BASIC CINNAMON FLAVOR USING CIS-BETA-CYCLOHOMOCITRAL ENOL BUTYRATE

The following basic cinnamon flavor is prepared:

| Ingredient | Parts by Weight |
| --- | --- |
| Cassia oil | 10.0 |
| Cinnamaldehyde | 70.0 |
| Cinnamyl formate | 0.5 |
| Cuminic aldehyde | 0.2 |
| Eugenol | 14.0 |
| Furfural | 0.2 |
| Methyl cinnamate | 2.5 |
| Caryophyllene | 2.6 |

The formulation is divided into two equal parts. To the first part, at the rate of 10 ppm cis beta-cyclohomocitral enol isobutyrate prepared according to the process of Example XXXVII, is added in the form of a 5% solution in food grade 95% aqueous ethyl alcohol. The second part of the formulation has nothing additional added thereto. The flavor formulation containing the cis beta-cyclohomocitral enol isobutyrate has more of the desired woody/powdery, delicate, sweet aroma and taste characteristics not found in the basic flavor formulation. Therefore, it is preferred over the flavor formulation which does not contain the said beta-cyclohomocitral enol isobutyrate.

EXAMPLE XLI

BASIC RASPBERRY FORMULATION CONTAINING CIS BETA-CYCLOHOMOCITRAL ENOL BUTYRATE

The following basic raspberry formulation is prepared:

| Ingredient | Parts by Weight |
| --- | --- |
| Vanillin | 2 |
| Maltol | 4 |
| Parahydroxy benzyl acetone | 5 |
| Alpha-ionone (10% in propylene glycol) | 2 |
| Ethyl butyrate | 6 |
| Ethyl acetate | 16 |
| Dimethyl sulfide | 1 |
| Isobutyl acetate | 14 |
| Acetic acid | 10 |
| Acetaldehyde | 10 |
| Propylene glycol | 930 |

The foregoing formulation is divided into two parts. To the first part is added cis beta-cyclohomocitral enol butyrate prepared according to the process of Example XXXV at the rate of 100 ppm in the form of a 5% solution in food grade 95% aqueous ethanol. The second portion of the above formulation does not have any additional materials added thereto. The two formulations are compared. The formulation containing the cis isomer of beta-cyclohomocitral enol butyrate has a sweet, ripe raspberry aroma and a full, more ripe raspberry-like taste; and as such it is preferred over the formulation not containing said cis isomer of beta-cyclohomocitral enol butyrate.

EXAMPLE XLII

FLAVOR USE OF CIS BETA-CYCLOHOMOCITRAL ENOL OCTANOATE

At the rate of 3 ppm cis beta-cyclohomocitral enol octanoate, prepared according to the process of Example XXXVIII, is added to a standard instant tea formulation. The instant tea is made up into a tea beverage by means of the addition of boiling water thereto. The stale, bitter, tannin notes of the hot tea are substantially improved by means of the addition of the cis isomer of beta-cyclohomocitral enol octanoate. Fruity/delicate rosey, pleasant tea-like aroma notes and fruity/delicate rosey/tea taste notes are added to the basic tea taste and aroma by means of the cis isomer of beta-cyclohomocitral enol octanoate.

EXAMPLE XLIII

FLAVOR USE OF THE TRANS ISOMER OF BETA-CYCLOHOMOCITRAL ENOL ISOBUTYRATE

At the rate of 3 ppm the trans isomer of beta-cyclohomocitral enol isobutyrate is added to a standard commercial instant tea vending machine product. Prior to addition the tea is not considered to have a pleasant tea-like aroma. The taste is stale and bitter with the tannin notes dominating. The addition of the trans isomer of beta-cyclohomocitral enol butyrate at the rate of 3 ppm to the bitter tea followed by the addition of boiling water in order to make a beverage, adds a light, fruity/apple, pleasant tea aroma to the beverage and improves the taste with delicate/fruity/tea-like notes.

EXAMPLE XLIV

USE OF THE TRANS ISOMER OF BETA-CYCLOHOMOCITRAL ENOL BUTYRATE IN BEVERAGE

At the rate of 1 ppm, the trans isomer of beta-cyclohomocitral enol butyrate prepared according to Example XXXVI is added to Hi-C Grape Drink (containing 10% grape juice) manufactured by the Coca Cola Corporation of Houston, Texas. The addition of the trans isomer of beta-cyclohomocitral enol butyrate to the Hi-C grape drink at the rate of 1 ppm in the form of a 1% propylene glycol solution improves the flat top notes of the drink adding a delicate concord grape flavor and a fuller taste thereto.

EXAMPLE XLV

BASIC CLOVE FORMULATION USING THE CIS ISOMER OF BETA-CYCLOHOMOCITRAL ENOL ACETATE

The following basic clove formulation is prepared:

| Ingredient | Parts by Weight |
| --- | --- |
| Vanillin | 2 |
| Caryophyllene | 8 |
| Guaiacol (10% solution in 95% aqueous food grade ethanol) | 1 |
| Cuminaldehyde | 1 |
| 5-Methyl furfural | 5 |
| Eugenol | 83 |

The above formulation is divided into two parts. To the first part is added at the rate of 5% the cis isomer of beta-cyclohomocitral enol acetate prepared according to the process of Example LVIII, infra. The second part of the above formulation does not have any additional ingredients added thereto. The use of the cis isomer of beta-cyclohomocitral enol acetate in this basic clove formulation causes the formulation to have added thereto dry-woody notes in aroma and taste. As a result of adding the cis isomer of beta-cyclohomocitral enol acetate, the clove aroma is more delicate, better rounded and therefore preferred as better and more characteristic.

EXAMPLE XLVI

PREPARATION OF TRANS BETA-CYCLOHOMOCITRAL ENOL PROPIONATE

Reaction

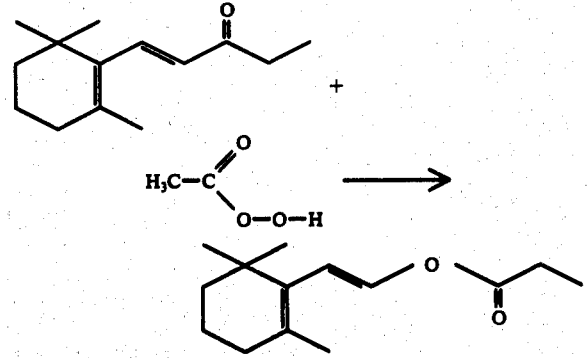

Into a 250 ml reaction flask equipped with stirrer, addition funnel, thermometer and cooling bath, the following materials are placed:

| Ingredients | Quantity |
| --- | --- |
| beta-n-methyl ionone (91% purity) | 22.6 g (0.1 mole) |
| water | 40 ml |
| acetic acid | 50 ml |
| sodium acetate | 17 g (0.17 mole) |

The reaction mass is stirred for a period of 10 minutes at room temperature at which time the addition of 24.0 g (0.13 mole) of a 40% solution of peracetic acid is commenced. The peracetic acid is added over a period of 15 minutes while the reaction mass is maintained at a temperature of 25°–30° C. After addition of the peracetic acid is completed, the reaction mass is stirred for a period of 2 hours while maintaining the temperature at 25°–30° C. The reaction mass is then added to 200 ml water and the resulting mixture is extracted with one 200 ml portion of methylene chloride and again with one 100 ml portion of methylene chloride. The methylene chloride extracts are combined with the organic phase and the combined extracts are washed with two 100 ml portions of water. The resulting material is dried over anhydrous magnesium sulfate, filtered and stripped of solvent on a Rotovap yielding 23 grams of product.

Figure 18:
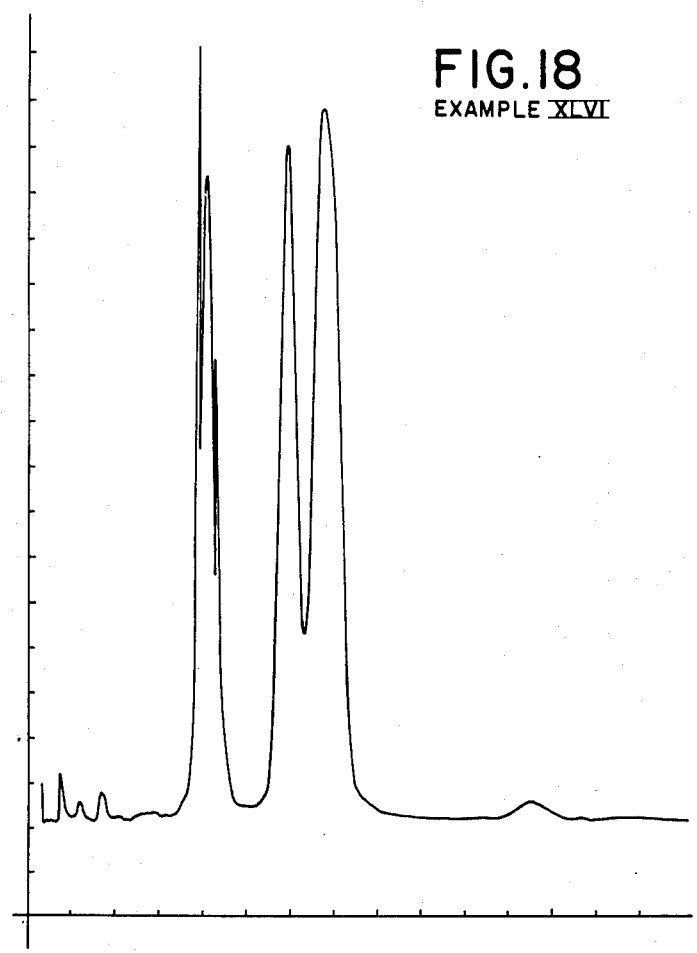
FIG. 18 is the GLC profile for the reaction product of Example XLVII wherein beta-cyclohomocitral enol propionate is produced.

The GLC profile of the reaction product containing trans beta-cyclohomocitral enol propionate is set forth in FIG. 18.

The trans beta-cyclohomocitral enol propionate insofar as its flavor is concerned has a sweet, floral, ionone-like, raspberry, dried fruit, tobacco-like aroma with a sweet, fruity, ionone, raspberry, dried fruit, tobacco flavor characteristic at 1 ppm. It is about two times as strong, sweeter, fruitier, and more raspberry-like than the trans beta-cyclohomocitral enol acetate.

Insofar as its perfumery properties are concerned the trans beta-cyclohomocitral enol propionate has a butyric/propionic acid topnote with tobacco, woody and ionone notes; but it is not as pleasant as trans beta-cyclohomocitral enol acetate which is preferred by a panel of perfumers.

EXAMPLE XLVII

ATTEMPTED PREPARATION OF BETA-CYCLOHOMOCITRAL ENOL ACETATE USING PERMALEIC ACID ANHYDRIDE

Into a 500 ml flask equipped with ice bath, thermometer and magnetic stirrer are placed 150 ml methylene chloride and 38.5 g (0.34 moles) of 30% hydrogen peroxide. The resulting mixture is cooled to 0° C using the ice bath and 39.2 g (0.4 moles) of freshly crushed maleic anhydride is added to the mixture. The reaction mixture is stirred for one hour and is then brought to reflux. While refluxing 38.4 g (0.2 moles) of beta-ionone in 40 g of methylene chloride is added to the reaction mass over a one hour period. The reaction mass is then stirred for a period of two hours and now exists in two phases; an aqueous phase and an organic phase. The organic phase is separated and washed with one 150 ml portion of saturated sodium carbonate followed by one 150 ml portion of saturated sodium chloride solution. The organic phase is then dried over anhydrous magnesium sulfate and stripped on a Rotovap to yield 37 g of crude product. GLC analysis of the crude material indicates a 97.5% yield of beta-ionone epoxide. At best, there is only a trace of beta-cyclohomocitral enol acetate present in the reaction product.

EXAMPLE XLVIII

PRODUCTION OF BETA-CYCLOHOMOCITRAL ENOL ACETATE USING METHYLENE DICHLORIDE SOLVENT

Reaction:

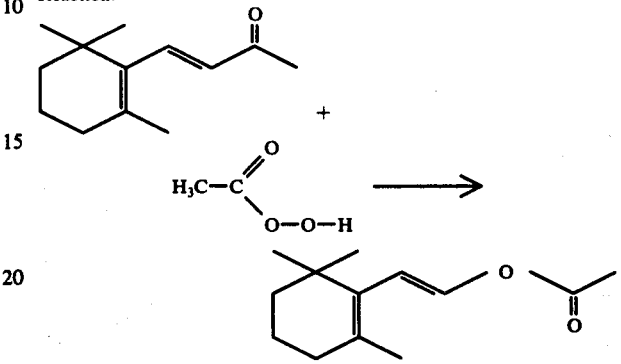

Into a 250 ml reaction flask equipped with stirrer, thermometer, cooling bath and addition funnel the following materials are added:

| Ingredients | Quantity |
| --- | --- |
| Methylene dichloride | 100 ml |
| Beta-ionone | 19.2 g (0.1 mole) |
| Sodium acetate | 13 g (0.13 mole) |

The reaction mass is stirred at room temperature for a period of 10 minutes, after which period of time addition of 19.2 g (0.10 mole) of 40% peracetic acid is commenced with a reaction exotherm noted. The addition of the peracetic acid takes place over a period of 45 minutes at a temperature from about 25° up to 30° C. After the 45 minute period of addition, the reaction mass is stirred for 1.5 hours. A sample taken at this point indicates a ratio of beta-cyclohomocitral enol acetate:-beta-iononeepoxide of 1:1. Stirring is continued for another 2.25 hours at which time GLC indicates the same ratio of enol acetate:epoxide.

At the end of 3.75 hours the reaction mass is added to 100 ml water yielding 2 phases; an organic phase and an aqueous phase. The aqueous phase is separated from the organic phase and the organic phase is washed with three 100 ml portions of water. The organic phase is then dried over anhydrous magnesium sulfate, filtered and stripped on a Rotovap yielding 10.5 grams of an oil. GLC analysis of the crude product indicates:

| Ingredients | Quantity |
| --- | --- |
| beta-cyclohomocitral | 0.5%% |
| trans beta-cyclohomocitral enol acetate | 21% |
| unreacted beta-ionone | 33% |
| beta-ionone epoxide | 42% |

Figure 19:
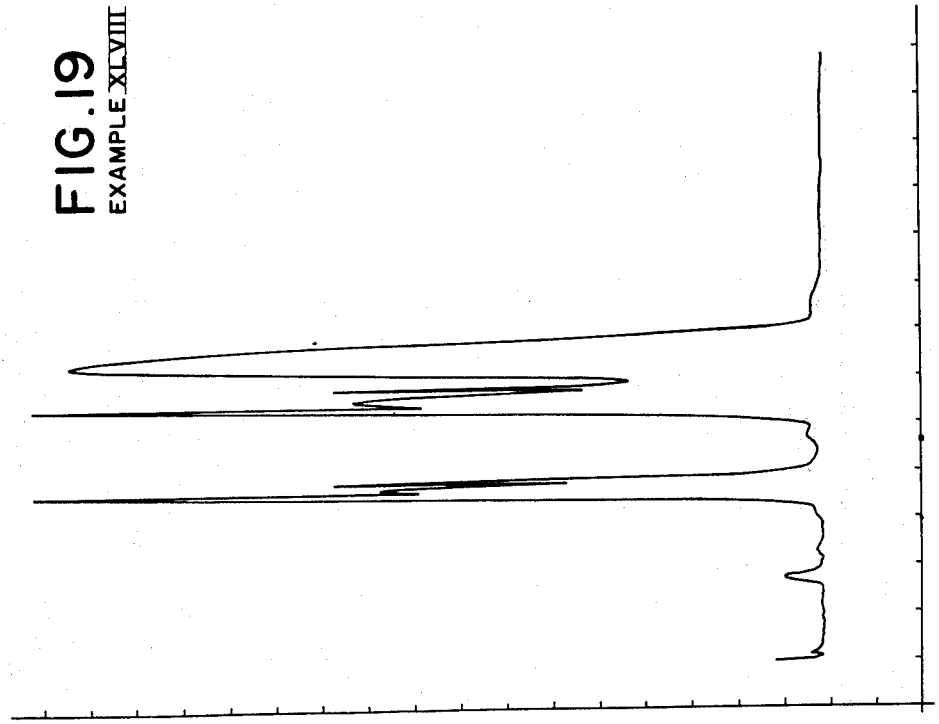
FIG. 19 is the GLC profile for the reaction product of Example XLVIII wherein beta-cyclohomocitral enol acetate is produced.

The yield of beta-cyclohomocitral enol acetate is thus determined to be about 20% with percent conversion from beta-ionone to enol acetate of about 30%. Figure 19 sets forth the GLC profile for the crude reaction product.

EXAMPLE XLIX

PRODUCTION OF TRANS BETA-CYCLOHOMOCITRAL ENOL ACETATE USING A BENZENE SOLVENT

Into a 500 ml reaction flask equipped with stirrer, thermometer and addition funnel the following materials are added:

| Ingredients | Quantity |
|---|---|
| anhydrous benzene | 100 ml |
| beta-ionone | 19.2 g (0.1 mole) |
| sodium acetate | 13 g (0.13 mole) |

The reaction mass is stirred for a period of 10 minutes at room temperature. At this point addition of 19.2 g (0.10 mole) of 40% peracetic acid is commenced and continued for a period of 30 minutes while maintaining the reaction mass temperature at 25°–30° C. The reaction mass is then stirred for another 3 hours at which time it is added to 150 ml of saturated sodium chloride solution. 50 ml of methylene chloride is then added to the resulting mixture. The organic phase is separated from the aqueous phase and the organic phase is washed with one 100 ml portion of saturated aqueous sodium chloride and one 100 ml portion of water. The organic phase is then dried over anhydrous magnesium sulfate, filtered and stripped on a Rotovap to yield 22.8 g of an oil. GLC analysis of the crude product indicates:

| Ingredients | Quantity |
|---|---|
| trans beta-cyclohomocitral enol acetate | 25.0% (27.4% yield) |
| beta-ionone | 27.5% (32.6% recovery) |
| beta-ionone epoxide | 36.1% (39.5% yield) |

Figure 20:
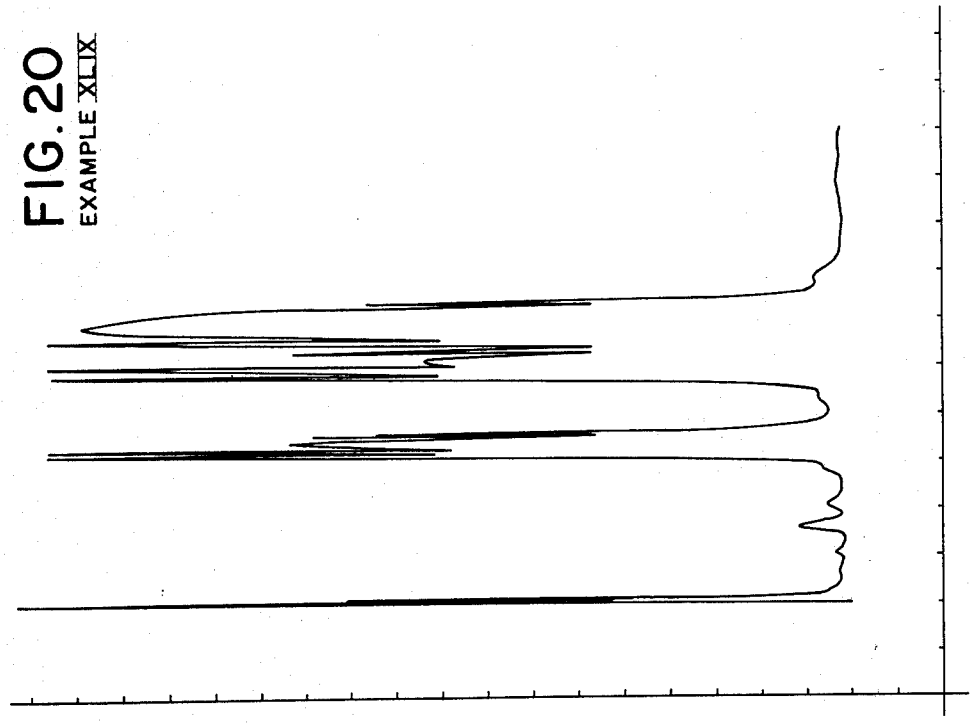
FIG. 20 is the GLC profile for the reaction product of Example XLIX wherein beta-cyclohomocitral enol acetate is produced.

Based on the foregoing results the yield of trans beta-cyclohomocitral enol acetate is 27.4%. FIG. 20 illustrates the GLC profile of the crude reaction product.

EXAMPLE L

PREPARATION OF BETA-CYCLOHOMOCITRAL ENOL ACETATE USING BENZENE SOLVENT AND M-CHLOROPERBENZOIC ACID OXIDIZING AGENT

Reaction:

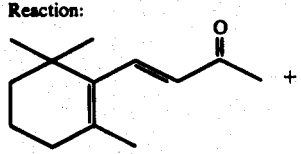

-continued

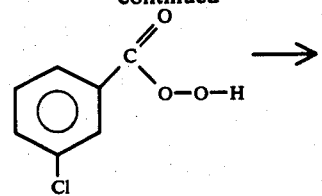

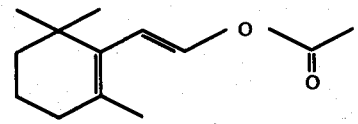

Into a 500 ml reaction flask equipped with stirrer, thermometer and addition funnel the following materials are added:

| Ingredients | Quantity |
|---|---|
| Benzene | 100 ml |
| Sodium acetate | 13 g (0.13 mole) |
| Beta-ionone | 19.2 g (0.10 mole) |

The reaction mass is stirred for 10 minutes at which time addition of 21.4 g (0.1 mole) of 85% m-chloroperbenzoic acid is commenced. Addition of the m-chloroperbenzoic acid is carried out for a period of 80 minutes while maintaining the temperature at 25°–30° C. At the end of the 80 minute period the reaction mass is stirred for an additional 2 hours at which time the solids are filtered from the reaction mass. The organic layer is then washed with one 100 ml portion of water, dried over anhydrous magnesium sulfate, filtered and stripped of solvent on a Rotovap to yield 21.9 g of an oil. GLC analysis of the crude oil indicates:

| Ingredients | Quantity |
|---|---|
| Trans beta-cyclohomocitral enol acetate | 28.3% (29.7% yield) |
| Beta-ionone | 22.6% (25.7% recovery) |
| beta-ionone epoxide | 37.8% (39.7% yield) |

FIG. 21 sets forth the GLC profile for the crude reaction product.

EXAMPLE LI

ATTEMPTED PRODUCTION OF BETA-CYCLOHOMOCITRAL ENOL ACETATE USING PERPHTHALIC ACID ANHYDRIDE OXIDIZING AGENT AND A CYCLOHEXANE SOLVENT

Reaction:

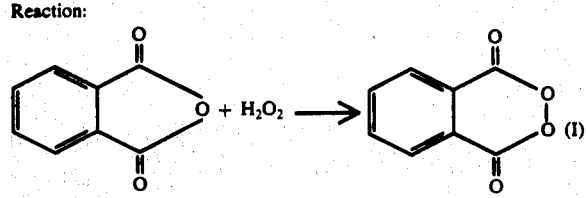

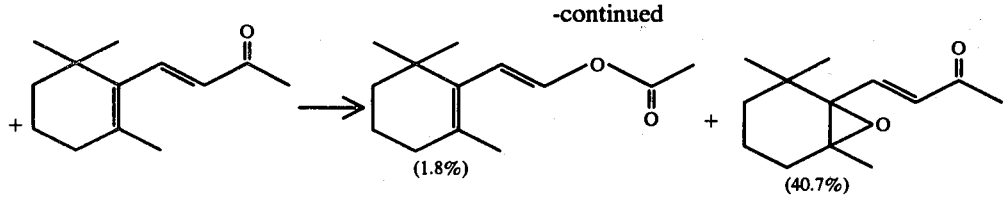

(1.8%)      (40.7%)

Into a 500 ml reaction flask equipped with stirrer, thermometer and addition funnel the following materials are added:

| Ingredients | Quantity |
| --- | --- |
| Cyclohexane | 150 ml |
| 30% Hydrogen peroxide | 19.2 g (0.17 mole) |

The reaction mass is cooled to 0° C and, 19.6 (0.2 mole) of perphthalic anhydride is added slowly. The reaction mass is then stirred for one hour after which period of time 19.2 g of beta-ionone in 50 ml cyclohexane is added over a period of 30 minutes at about 25° C. At the end of the 30 minute addition period, the reaction mass is stirred for a period of 3 hours and then added to 150 ml water. The solids are filtered and the organic layer is separated from the aqueous layer. The organic layer is washed with one 100 ml portion of saturated aqueous salt solution and is dried over anhydrous magnesium sulfate, filtered and stripped of solvent on a Rotovap yielding 20.0 g of an oil. GLC analysis of the crude oil indicates:

| Ingredients | Quantity |
| --- | --- |
| Trans beta-cyclohomocitral enol acetate | 1.8% (1.8% yield) |
| Beta-ionone | 47.3% (51.4% recovery) |
| Beta-ionone epoxide | 40.7% (40.9% yield) |

The foregoing represents 1.8% yield of trans beta-cyclohomocitral enol acetate. FIG. 22 sets forth the GLC profile for the crude reaction product.

EXAMPLE LII

ATTEMPTED PRODUCTION OF BETA-CYCLOHOMOCITRAL ENOL ACETATE USING A DIMETHYL ANILINE SOLVENT

Into a 500 ml reaction flask equipped with stirrer, thermometer and addition funnel the following materials are placed:

| Ingredients | Quantity |
| --- | --- |
| Dimethyl aniline | 100 ml |
| Beta-ionone | 19.2 g (0.1 mole) |
| Sodium acetate | 13 g (0.13 mole) |

The reaction mass is stirred for a period of 10 minutes after which time addition of 19.2 g (0.01 mole) of 40% peracetic acid is commenced while maintaining the reaction mass at a temperature in the range of 25°-30° C.

Additional of peracetic acid takes place over a period of 30 minutes with stirring while maintaining the temperature of the reaction mass at 25°-30° C. After addition of the peracetic acid the reaction mass is stirred for another 2 hours. At this point the reaction mass has a characteristic purple color.

The reaction mass is then added to 300 ml water and the resulting mixture is added to 300 ml diethyl ether thereby forming an emulsion. The resulting emulsion is broken upon heating and standing for a period of about 2 hours. The ether layer is separated from the aqueous layer and GLC analysis is carried out on the ether layer. GLC analysis indicates traces of beta-cyclohomocitral enol acetate and beta-ionone epoxide. The aqueous layer is purplish indicating that the amine is oxidized preferentially over the beta-ionone.

The GLC profile for the reaction product in the ether layer is set forth in FIG. 23.

EXAMPLE LIII

PRODUCTION OF BETA-CYCLOHOMOCITRAL ENOL ACETATE USING FORMAMIDE

Reaction:

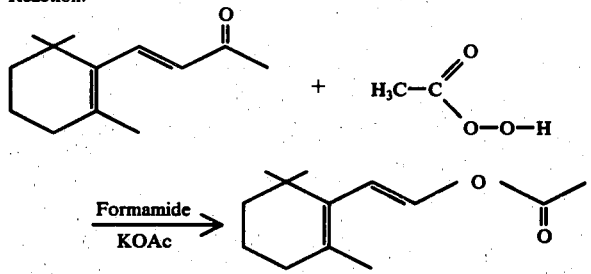

Into a 500 ml reaction flask equipped with stirrer, thermometer and addition funnel the following materials are placed:

| Ingredients | Quantity |
| --- | --- |
| Formamide | 100 ml |
| Potassium acetate | 13 g (0.13 mole) |
| Beta-ionone | 19.2 g (0.1 mole) |

The resulting mixture is stirred for 10 minutes. At the end of the 10 minute period, addition of 19.6 g (0.1 mole) of 40% peracetic acid is commenced while maintaining the temperature at 25°-30° C. The reaction is mildly exothermic thus not requiring the use of a cooling bath. The addition of the peracetic acid is carried out for a period of 30 minutes. At the end of this 30 minute period, the reaction mass is stirred for another 2 hour period.

The reaction mass is then added to 200 ml water which, in turn, is added to 200 ml diethyl ether. An emulsion is formed which breaks upon heating and standing overnight.

GLC analysis of the ether layer indicates a major peak which is trans beta-cyclohomocitral enol acetate as well as smaller quantities of beta-ionone epoxide and beta-ionone. The aqueous and ether layer are separated and the ether layer is washed with one 100 ml portion of aqueous saturated sodium chloride solution. The ether layer is then dried over anhydrous magnesium sulfate, filtered and stripped of solvent on a Rotovap yielding 21.9 g of product. GLC analysis of the stripped crude product indicates the following materials to be present:

| Ingredients | Quantity and Yield |
|---|---|
| Beta-cyclohomocitral enol acetate | 9.7 g (46.6% yield) |
| Beta-ionone | 7.18 g (37.4% recovery) |
| Beta-ionone epoxide | 3 g (14.4% yield) |

The GLC profile of the crude reaction product is set forth in FIG. 24.

EXAMPLE LIV

PRODUCTION OF TRANS BETA-CYCLOHOMOCITRAL ENOL ACETATE USING DIMETHYL FORMAMIDE SOLVENT AND BUFFER

Into a 500 ml reaction flask equipped with stirrer, thermometer and addition funnel the following materials are added:

| Ingredients | Quantity |
|---|---|
| Dimethyl formamide | 100 ml |
| Beta-ionone | 19.2 g (0.1 mole) |
| Potassium acetate | 13 g (0.1 mole) |

The resulting mixture is stirred for a period of 10 minutes after which time addition of 19.6 g (0.1 mole) of 40% peracetic acid is commenced while maintaining the reaction mass at a temperature of 25°–30° C. The addition of the peracetic acid is carried out over a period of 50 minutes while maintaining the reaction mass at 25°–30° C. A very mild exotherm is noted. After addition of the peracetic acid is completed the reaction mass is stirred for an additional 2 hour period while maintaining the reaction mass at room temperature.

The reaction mass is then added to 200 ml water and 200 ml diethyl ether is added to the resulting mixture. The organic and aqueous layers are separated and the organic layer is washed with one 100 ml portion of aqueous saturated sodium chloride solution. The ether layer is then dried over anhydrous magnesium sulfate, filtered and stripped of solvent on a Rotovap yielding 20.1 g of an oil. GLC analysis of the stripped crude indicates the following materials to be present:

| Ingredients | Quantity |
|---|---|
| Beta-cyclohomocitral enol acetate | 4.26 (20.4% yield) |
| Beta-ionone | 10.8 g (56% recovery) |
| Beta-ionone epoxide | 13% yield |

Figure 25:
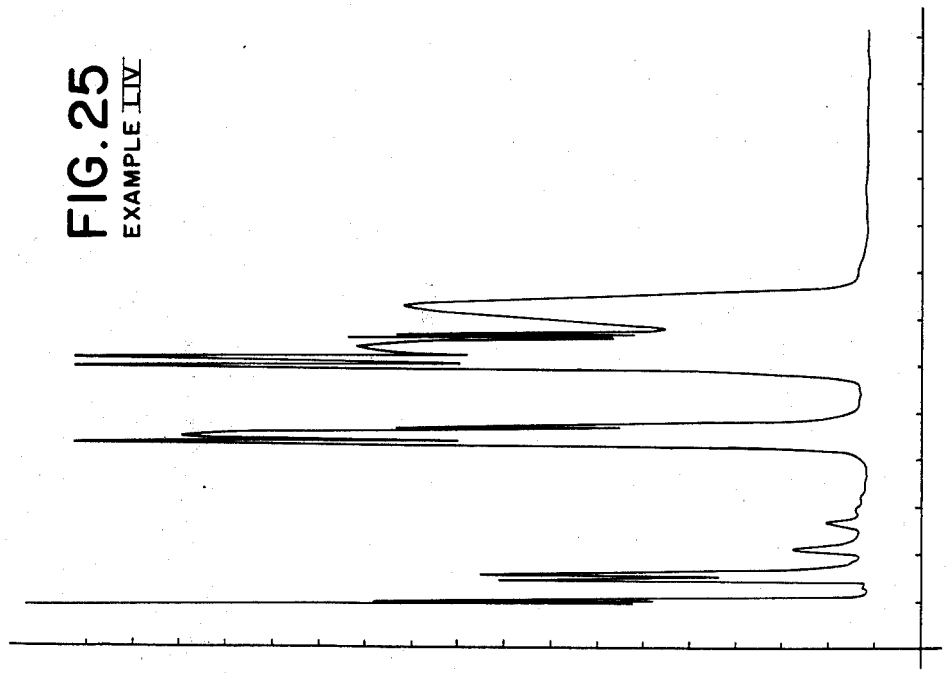
FIG. 25 is the GLC profile for the reaction product of Example LIV wherein beta-cyclohomocitral enol acetate is produced.

The GLC profile for the stripped crude product is set forth in FIG. 25.

EXAMPLE LV

PRODUCTION OF BETA-CYCLOHOMOCITRAL ENOL ACETATE USING m-CHLORO PERBENZOIC ACID OXIDIZING AGENT (USING 50% MORE SOLVENT THAN IN EXAMPLE L)

Reaction:

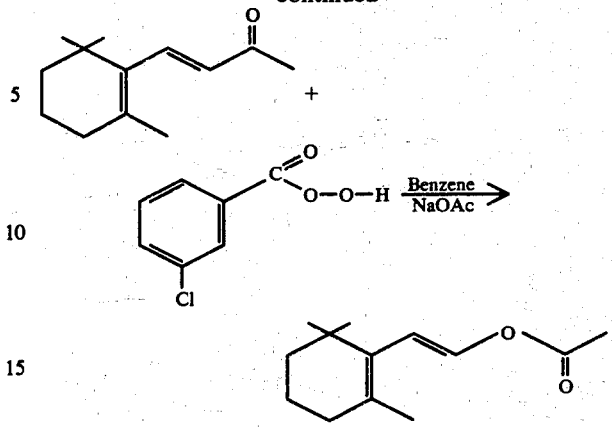

Into a 500 ml reaction flask equipped with stirrer, thermometer and reflux condenser are placed the following materials:

| Ingredients | Quantity |
|---|---|
| Benzene | 150 ml |
| Sodium acetate | 13 g (0.13 mole) |
| Beta-ionone | 19.2 g (0.1 mole) |

The resulting mixture is brought to reflux at which point addition of 21.4 g (0.1 mole) of 85% m-chloro perbenzoic acid is commenced slowly. The addition takes place over an 80 minute period. At the end of this time the reaction mass is stirred at reflux for an additional 2 hours. The reaction mass is then added to 200 ml water thereby forming two phases; an aqueous phase and an organic phase. The aqueous phase is separated from the organic phase and 200 ml diethyl ether is added to the aqueous phase. The organic phase and ether washings are then combined and washed with one 100 ml portion of water. The resulting organic layer is dried over anhydrous magnesium sulfate and filtered. The resulting product weighs 302.2 g. This material is then stripped on a Rotovap yielding 38.2 g of a solid. GLC analysis indicates:

| Ingredients | Quantity |
|---|---|
| Beta-cyclohomocitral enol acetate | 4.2 g (20%) |
| Beta-ionone | 6.1 g (32%) |
| Beta-ionone epoxide | 13 g (62%) |

Figure 26:
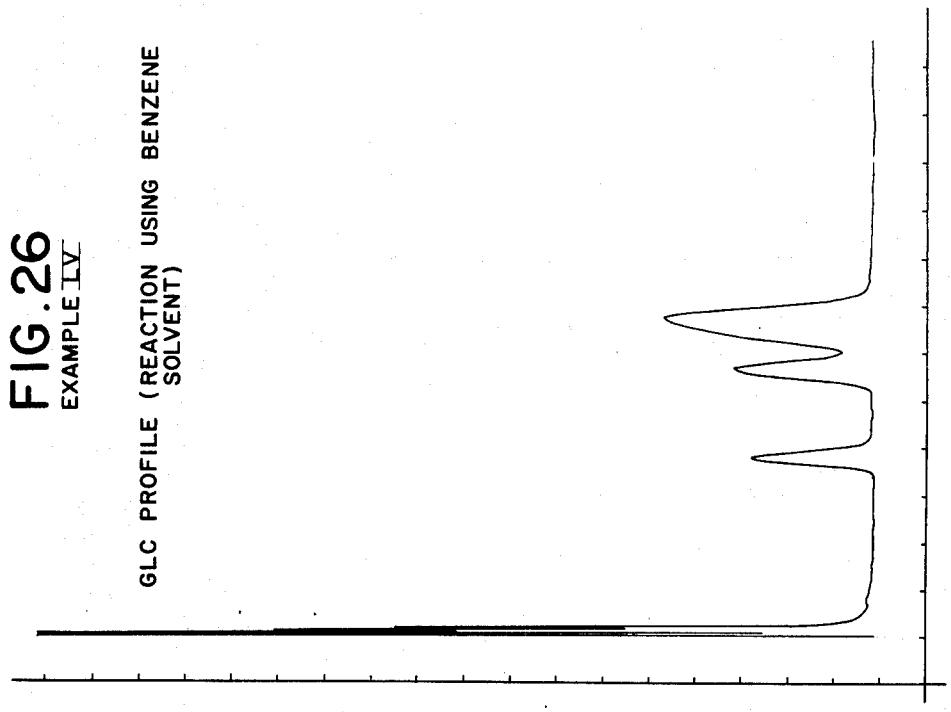
FIG. 26 is the GLC profile for the reaction product of Example LV wherein beta-cyclohomocitral enol acetate is produced.

The GLC profile is set forth in FIG. 26.

EXAMPLE LVI

PRODUCTION OF TRANS BETA-CYCLOHOMOCITRAL ENOL ACETATE USING A FORMAMIDE SOLVENT

A procedure is carried out identical to that of Example LIII except that the resulting crude product weighs 26.4 g and the GLC analysis of the stripped product indicates:

| Ingredients | Quantity |
|---|---|
| Trans beta-cyclohomocitral enol acetate | 12.2 g (59%) |
| Beta-ionone | 3.0 g (16%) |
| Beta-ionone epoxide | 7.2 g (34%) |

The GLC profile is set forth in FIG. 27.

EXAMPLE LVII

OXIDATION OF DELTA METHYL IONONE TO FORM CORRESPONDING TRANS ENOL ACETATE

Reaction:

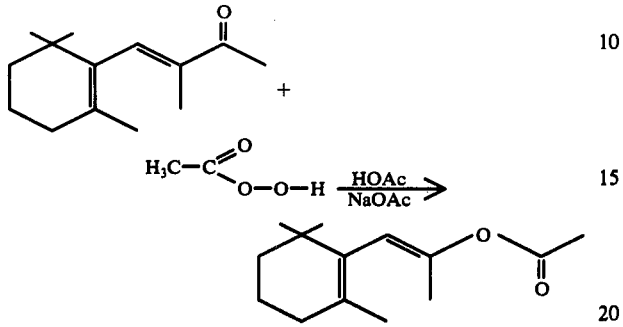

Into a 250 ml reaction flask equipped with stirrer, addition funnel, thermometer and cooling bath the following materials are placed:

| Ingredients | Quantity |
| --- | --- |
| Delta methyl ionone | 24.8 (0.1 mole) |
| Water | 40 ml |
| Acetic acid | 50 ml |
| Sodium acetate | 17 g (0.17 mole) |

The resulting mixture is stirred for 10 minutes at which point in time addition of 24 g (0.13 mole) of 40% peracetic acid is commenced while maintaining the reaction mass at a temperature of 25°–30° C. Addition of the peracetic acid takes place over a ten minute period. The reaction is mildly exothermic. After addition of the peracetic acid is completed, the reaction mass is stirred for another 2 hours at 25°–30° C. At the end of the 2 hour period the reaction mass is added to 200 ml water and the resulting material is extracted with one 200 ml portion of methylene dichloride followed by one 100 ml portion of methylene dichloride. The methylene dichloride extracts are combined and washed with two 100 ml portions of water. The washed methylene dichloride extracts are combined and dried over anhydrous magnesium sulfate, filtered and stripped on a Rotovap thus yielding 26.3 g of a crude product. GLC analysis of the crude product indicates two early eluting peaks, a relatively small amount of starting material and two new later eluting peaks. The second early eluting peak is the enol acetate having the structure:

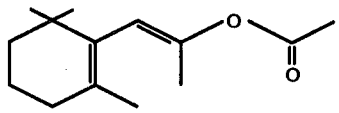

The GLC profile for the resulting crude product is set forth in FIG. 28.

From a flavor standpoint, the alpha, 2,6,6-trimethyl-1-cyclohexene-trans-1-ethenyl acetate has a woody, ionone-like, gasoline-like, tomato aroma with a woody, ionone, gasoline-like solvent flavor character at 1 ppm. From a fragrance standpoint the said compound has an oily, woody, musky, butyric, ionone-like note and is not as sweet or fruity or berry-like as beta-cyclohomocitral enol acetate. On dry out, the resulting compound has a woody and burnt aroma.

EXAMPLE LVIII

PREPARATION OF BETA-CYCLOHOMOCITRAL CIS ENOL ACETATE

Reaction:

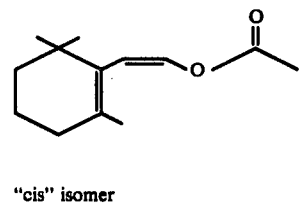

Into a 100 ml reaction flask equipped with stirrer, thermometer and reflux condenser are placed the following ingredients:

| Ingredients | Quantity |
| --- | --- |
| beta-cyclohomocitral | 16.6 g (0.1 mole) |
| acetic anhydride | 17.3 g (0.17 mole) |
| potassium acetate | 0.1 g (0.01 mole) |

The reaction mass is refluxed with stirring, for a period of 9 hours. At the end of the 9 hours period, 50 ml diethyl ether is added to the reaction mass. The reaction mass is then washed neutral with five 50 ml portions of water. The resulting material is then dried over anhydrous magnesium sulfate, filtered and stripped of solvent on a Rotovap. GLC analysis indicates the presence of 3 compounds:
1. beta-cyclohomocitral
2. beta-cyclohomocitral trans enol acetate
3. beta-cyclohomocitral cis enol acetate The GLC profile is set forth in FIG. 29. The GC-MS profile is set forth in FIG. 30. The NMR spectrum for the trapping consisting of the cis enol acetate is given in FIG. 31. The NMR analysis is as follows:

| Peak | Interpretation | |
| --- | --- | --- |
| 0.98 ppm (s) | CH₃\C—/CH₃ | 6H |
| 1.54 (broad singlet) | =C—CH₃ | 3H |
| 2.14 (s) | CH₃—C(=O)— | 3H |
| 5.34 (d) | | 1H |

-continued

| Peak | Interpretation |
|---|---|
| 7.04 (d) | } olefinic protons |

It is noteworthy that the olefinic protons of the trans isomer are at 5.75 ppm and 6.98 ppm.

The resulting material, the beta-cyclohomocitral cis enol acetate, has the following organoleptic properties:

| Flavor Properties | Perfumery Properties |
|---|---|
| A sweet, floral, ionone-like, woody, violet, fruity, caryophyllene aroma with hay-like, ionone-like, woody, violet, caryophyllene-like, tobacco and cedarwood-like flavor characteristics at 5 ppm. | Earthy, camphoraceous and sea-like aroma with ionone and fruity nuances in addition to sweet, beta-ionone-like, tobacco and fruity nuances. |

EXAMPLE LIX

ATTEMPTED PREPARATION OF BETA-CYCLOHOMOCITRAL ENOL ACETATE USING DIMETHYL FORMAMIDE SOLVENT BUT NO BUFFER

Into a 500 ml reaction flask equipped with stirrer, thermometer and addition funnel are added the following materials:

| Ingredients | Quantity |
|---|---|
| dimethyl formamide | 100 ml |
| beta-ionone | 19.2 g |

With stirring over a period of 30 minutes while maintaining the contents of the 500 ml reaction flask at 25° C, 19.6 g (0.1 mole) of 40% peracetic acid is added to the reaction mass. At the end of the 30 minute period stirring is ceased and the reaction mass is allowed to stand for a period of 144 hours. At the end of the 144 hour period 200 ml water is added to the reaction mass, followed by 200 ml diethyl ether, with stirring. An emulsion forms which separates into two layers; an aqueous layer and an organic layer. The aqueous layer is extracted with one 200 ml portion of diethyl ether. The ether washing is combined with the organic layer and the resulting solution is washed with one 200 ml portion of aqueous saturated sodium chloride solution. The organic layer is then dried over anhydrous magnesium sulfate, filtered and stripped of solvent on a Rotovap yielding 34.5 g of an oil.

GLC analysis of the stripped crude indicates that the ratio of beta-ionone to beta-ionone-epoxide is approximately 1:2 and that only a trace of beta-cyclohomocitral enol acetate is present.

EXAMPLES LX-LXIV

PRODUCTION OF BETA-CYCLOHOMOCITRAL ENOL ACETATE USING VARIOUS CONDITIONS

Examples LX-LXIV are carried out in a reaction flask equipped with stirrer, thermometer and addition funnel using a procedure similar to that of Example LIII. The reaction conditions and results are set forth in the following table:

| Example No. | Reaction Ingredients | Reaction Temperature | Products of Reaction |
|---|---|---|---|
| LX | 400 ml water, 26 g sodium acetate, 38.4 g (0.2 moles) beta-ionone, 76 g (0.4 moles) 40% peracetic acid | 0° C for 3 hours | beta-cyclohomocitral enol acetate 4.2%, beta-ionone 47%, beta-ionone epoxide 39% |
| LXI | 80 ml water, acetic acid 100 ml, sodium acetate 34 g, beta-ionone 38.4 g (0.2 moles), 76 g (0.4 moles) 40% peracetic acid | 0 to −5° C for 5 hours | beta-cyclohomocitral enol acetate 46.8%, beta-ionone 10.3%, beta-ionone epoxide 44.9% |
| LXII | formamide 180 ml, sodium acetate 26 g, beta-ionone 38.4 g (0.2 moles), 76 g (0.4 moles 40% peracetic acid | 0 to −5° C for 5 hours | beta-cyclohomocitral enol acetate 50.7%, beta-ionone 36.2%, beta-ionone epoxide 15.9% |
| LXIII | formamide 4500 ml, sodium acetate 650 g, beta-ionone 960 g, 40% peracetic acid 1900 g (10 moles) | 0° C for 3.5 hours | beta-cyclohomocitral enol acetate 52.6%, beta-ionone 15.6%, beta-ionone epoxide 25% |
| LXIV | formamide 400 ml, beta-ionone 38.4 g, potassium acetate (0.2 moles), 76 g (0.4 moles) 40% peracetic acid | 25° C for 3 hours | beta-cyclohomocitral enol acetate 43%, beta-ionone 1.8%, beta-ionone epoxide 43% |

EXAMPLE LXV

PREPARATION OF BETA-CYCLOHOMOCITRAL ENOL LAURATE

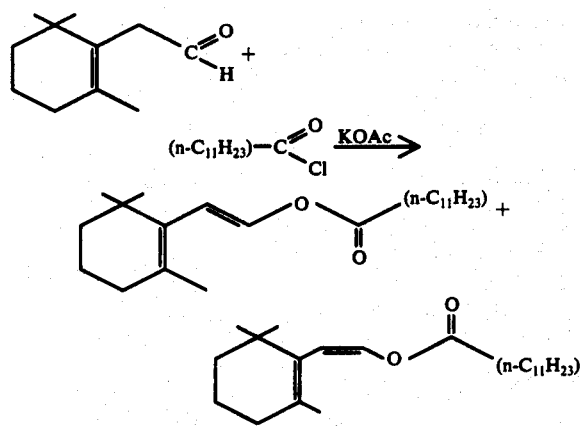

Into a 50 ml reaction flask equipped with thermometer, heating mantle and magnetic stirrer the following materials are charged:

| Ingredients | Quantity |
|---|---|
| lauroyl chloride | 15.8 g (.076 mole) |
| beta-cyclohomocitral | 7.3 g (.045 mole) |
| potassium acetate | 1 gram |

The reaction mass is heated for a period of 5 hours at a temperature in the range of from 160°–200° C. Upon heating, the reaction mass first turns a light purplish color and then a green color and evolution of hydrogen chloride gas is observed. The reaction mass is then cooled and poured into 200 ml water. The resulting aqueous phase is then extracted with two 150 ml portions of methylene chloride. The organic layers are combined and then dried over anhydrous magnesium sulfate, filtered and stripped of solvent on a Rotovap to yield 22.5 of a dark solid. GLC analysis of the stripped crude indicates an acid peak and 3 new peaks having a later retention time.

The GLC profile for the reaction product is set forth in FIG. 35. The GC-MS profile for the reaction product is set forth in FIG. 36.

EXAMPLE LXVI

TOBACCO FORMULATION

A tobacco mixture is produced by admixing the following ingredients:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 or 1,000 ppm of beta-cyclohomocitral enol butyrate produced according to the process of Example XXV. The control cigarettes not containing the trans beta-cyclohomocitral enol butyrate produced according to the process of Example XXXV and the experimental cigarettes which contain the trans beta-cyclohomocitral enol butyrate produced according to the process of Example XXV are evaluated by paired comparison and the results are as follows:

The experimental cigarettes are found to have a sweet, floral, tea-tobacco-like, fruity, damascenone aroma, prior to, and, on smoking. In addition, the natural tobacco taste and aroma is enhanced on smoking, as a result of using the trans beta-cyclohomocitral enol butyrate.

All cigarettes are evaluated for smoke flavor with a 20 mm cellulose acetate filter.

EXAMPLE LXVII

TOBACCO FORMULATION

A tobacco mixture is produced by admixing the following ingredients:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 or 1,000 ppm of cis beta-cyclohomocitral enol octanoate produced according to the process of Example XXVIII. The control cigarettes not containing the cis beta-cyclohomocitral enol octanoate produced according to the process of Example XXXVIII and the experimental cigarettes which contain the cis beta-cyclohomocitral enol octanoate produced according to the process of Example XXVIII are evaluated by paired comparison and the results are as follows:

The experimental cigarettes are found to have more body and to be sweeter, more aromatic, more tobacco-like and to have better mouthfeel than the control cigarettes.

The tobacco of the experimental cigarettes, prior to, and, on smoking, has sweet, slightly sour, cool-minty-like notes with pungent, waxy and natural tobacco-like nuances.

All cigarettes are evaluated for smoke flavor with a 20 mm cellulose acetate filter.

EXAMPLE LXVIII

TOBACCO FORMULATION

A tobacco mixture is produced by admixing the following ingredients:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 or 1,000 ppm of trans beta-cyclohomocitral enol octanoate produced according to the process of Example XXVIII. The control cigarettes not containing the trans beta-cyclohomocitral enol octanoate produced according to the process of Example XXXVIII and the experimental cigarettes which contain the trans beta-cyclohomocitral enol octanoate produced according to the process of Example XXVIII are evaluated by paired comparison and the results are as follows:

The experimental cigarettes are found to have more body and to be sweeter, more aromatic, more tobacco-like and to have better mouthfeel than the control cigarettes.

The tobacco of the experimental cigarettes, prior to, and, on smoking, has sweet, slightly sour, cool-minty-like notes with pungent, waxy and natural tobacco-like nuances.

All cigarettes are elevated for smoke flavor with a 20 mm cellulose acetate filter.

EXAMPLE LXIX

TOBACCO FORMULATION

A tobacco mixture is produced by admixing the following ingredients:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 or 1,000 ppm of cis beta-cyclohomocitral enol acetate produced according to the process of Example LVIII. The control cigarettes not containing the cis beta-cyclohomocitral enol acetate produced according to the process of Example LVIII and the experimental cigarettes which contain the cis beta-cyclohomocitral enol acetate produced according to the process of Example LVIII are evaluated by paired comparison and the results are as follows:

The experimental cigarettes are found to have more body and to be sweeter, more aromatic, more tobacco-like and less harsh with sweet, floral and fruity notes. The tobacco of the experimental cigarettes, prior to smoking, has sweet, floral and fruity notes. All cigarettes are evaluated for smoke flavor with a 20 mm cellulose acetate filter.

The cis beta-cyclohomocitral enol acetate produced according to the process of Example LVIII enhances the tobacco like taste and aroma of the blended cigarette, imparting to it sweet, natural tobacco notes.

EXAMPLE LXX

A. SCALED UP PREPARATION OF BETA-CYCLOHOMOCITRAL ENOL ACETATE USING FORMAMIDE AS SOLVENT AND PERACETIC ACID OXIDIZING AGENT AT A REACTION TEMPERATURE OF 0° C

Into a 12 liter reaction flask equipped with stirrer, thermometer, addition funnel and dry ice/acetone cooling bath, the following materials are added:

| Ingredients | Quantity |
| --- | --- |
| Formamide | 4500 ml |
| Sodium Acetate | 650 gm (7.92 mole) |
| Beta-ionone | 960 gm (5.0 mole) |

The reaction mass is stirred with cooling until a temperature of 0° C is attained. At this time the addition of 1900 gm (10.0 moles) of 40% peracetic acid is commenced. The addition is carried out over a period of 3.5 hours while maintaining the temperature at 0° C. At the end of the addition period the reaction mass is stirred for an additional 3.5 hours at a temperature of 0° C. At the end of this period the reaction mass is transferred to a five gallon open head separatory funnel and to it is added 5 liters of warm water. The mass is extracted with three 1 liter portions of methylene chloride and the combined extracts are washed with three 1 liter portions of water. The combined extracts are then dried over anhydrous magnesium sulfate and filtered. The solvent is then stripped atmospherically through a 2 inch porcelain saddle column to a liquid temperature of 100° C. The residual oil is distilled at reduced pressure through a 2 inch procelain saddle column to yield 984 grams of an oil in seven fractions. GLC analysis of the individual fractions indicates:

| Ingredient | Quantity |
| --- | --- |
| Trans-beta-cyclohomo-citral enol acetate | (52.6% yield) |
| Beta-ionone | (15.6% recovery) |
| Beta-ionone epoxide | (25% side product) |

B. PREPARATION OF BETA-CYCLOHOMOCITRAL BY BASE-CATALYZED HYDROLYSIS OF BETA-CYCLOHOMOCITRAL ENOL ACETATE

Into a 5 liter reaction flask equipped with stirrer, thermometer, addition funnel and dry ice/acetone cooling bath, the following materials are added:

| Ingredient | Quantity |
| --- | --- |
| Water | 1665 ml |
| Methanol | 1665 ml |
| Sodium Carbonate | 500 gm (4.71 mole) |

The mixture is stirred for a short period of time. The addition of 984 grams of a mixture of beta-cyclohomocitral enol acetate, beta-ionone and beta-ionone epoxide from the above-mentioned distillation is then commenced. The mixture is added over a period of 45 minutes, while maintaining a temperature of 25°–30° C. At the end of the addition period, the mixture is allowed to stir for an additional 2 hours at 25°–30° C. At the end of this period the reaction mass is poured into a five gallon open head separatory funnel and to it are added 3 liters of water and 1 liter of chloroform. The organic layer which forms is collected. The aqueous layer is then extracted with two additional 1 liter portions of chloroform. The organic extracts are combined, washed with two 1 liter portions of a saturated salt solution, dried over anhydrous magnesium sulfate and filtered. The organic layer is then subjected to a combined stripping and rushover at reduced pressure through a 2 inch porcelain saddle column to yield 758 grams of an oil. The oil is then distilled through an 18 inch Goodloe column at reduced pressure to yield 686 grams of an oil in fourteen fractions. A residue of 44 grams, containing beta-ionone and beta-ionone epoxide remains, due to column hold-up. GLC analysis of these fractions indicates:

| Ingredient | Quantity |
| --- | --- |
| Beta-cyclohomocitral | 583 gram (70% yield from beta-ionone) |
| Beta-ionone | 88 gram (9% recovery) |
| Beta-ionone epoxide | 9 gram (0.8% carried over side product |

What is claimed is:
1. "Cis" or "trans" or mixtures of "cis" and "trans" 2(2,2,6-trimethyl-1-cyclohexen-1-yl)ethen-1-ol ester defined by the structure:

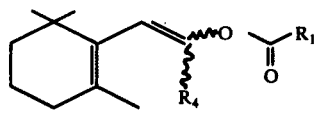

wherein $R_1$ is $C_1$-$C_{11}$ alkyl and $R_4$ is hydrogen or methyl.
2. A compound of claim 1, wherein $R_1$ is methyl and $R_4$ is hydrogen.
3. The compound of claim 2 wherein the ester moiety is in a "cis" relationship to the cyclohexyl moiety.
4. The compound of claim 2 wherein the ester moiety is in a "trans" relationship to the cyclohexenyl moiety.
5. The compound of claim 1 wherein $R_1$ is n-propyl, and $R_4$ is hydrogen.
6. The compound of claim 1 wherein $R_1$ is n-heptyl and $R_4$ is hydrogen.
7. The compound of claim 1 wherein $R_1$ is 2-propyl and $R_4$ is hydrogen.
8. The compound of claim 1 wherein $R_1$ and $R_4$ are each methyl, and the ester moiety is in a trans relationship to the cyclohexenyl moiety.
9. The compound of claim 1 wherein $R_1$ is n-$C_{11}H_{23}$ and $R_4$ is hydrogen.

* * * * *